United States Patent
Kitamura

(10) Patent No.: US 9,683,105 B2
(45) Date of Patent: Jun. 20, 2017

(54) PHOTOLUMINESCENT PIGMENT, AND PHOTOLUMINESCENT PAINT COMPOSITION AND AUTOMOBILE OUTER PANEL COATING MATERIAL CONTAINING SAME

(71) Applicant: Nippon Sheet Glass Company, Limited, Tokyo (JP)

(72) Inventor: Takeaki Kitamura, Sagamihara (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 326 days.

(21) Appl. No.: 14/363,658

(22) PCT Filed: Dec. 7, 2012

(86) PCT No.: PCT/JP2012/081848
§ 371 (c)(1),
(2) Date: Jun. 6, 2014

(87) PCT Pub. No.: WO2013/085049
PCT Pub. Date: Jun. 13, 2013

(65) Prior Publication Data
US 2014/0335348 A1    Nov. 13, 2014

(30) Foreign Application Priority Data

Dec. 9, 2011 (JP) ................. 2011-270444

(51) Int. Cl.
*C09C 3/06* (2006.01)
*C09D 5/22* (2006.01)
(Continued)

(52) U.S. Cl.
CPC ............ *C09C 3/063* (2013.01); *A61K 8/0258* (2013.01); *C03C 17/25* (2013.01); *C08K 9/02* (2013.01);
(Continued)

(58) Field of Classification Search
None
See application file for complete search history.

(56) References Cited

U.S. PATENT DOCUMENTS 6,045,914 A    4/2000  Sullivan et al.
7,604,862 B2 * 10/2009 Ambrosius ........... C09C 1/0024
                                          252/301.6 R
(Continued)

FOREIGN PATENT DOCUMENTS

CN    1654548    8/2005
CN    101104748  1/2008
(Continued)

OTHER PUBLICATIONS

Office Action issued in corresponding Japan Application No. 2013-548320, Jun. 16, 2016, 3 pages.
(Continued)

*Primary Examiner* — Alexandre Ferre
(74) *Attorney, Agent, or Firm* — Hamre, Schumann, Mueller & Larson, P.C.

(57) ABSTRACT

A bright pigment of the present invention is a bright pigment including flaky particles and a metal oxide layer covering each surface of the flaky particles. The bright pigment has a particle diameter corresponding to a 90% volume-cumulative particle diameter from a small particle diameter side, in a particle size distribution, of 55 µm or less. The flaky particles are formed of a material having a refractive index of 1.4 to 1.8. The flaky particles have an average thickness of 0.35 to 0.55 µm and substantially do not contain flaky particles having a thickness of 0.15 µm or less.

14 Claims, 2 Drawing Sheets

(51) Int. Cl.
| | |
|---|---|
| *C09C 1/00* | (2006.01) |
| *C09C 1/40* | (2006.01) |
| *C09C 1/28* | (2006.01) |
| *A61K 8/02* | (2006.01) |
| *C03C 17/25* | (2006.01) |
| *C08K 9/02* | (2006.01) |
| *C09D 7/12* | (2006.01) |
| *C09D 5/36* | (2006.01) |
| *B05D 5/06* | (2006.01) |
| *B05D 7/14* | (2006.01) |

(52) U.S. Cl.
CPC .......... *C09C 1/0015* (2013.01); *C09C 1/0021* (2013.01); *C09C 1/0081* (2013.01); *C09C 1/28* (2013.01); *C09C 1/40* (2013.01); *C09C 1/405* (2013.01); *C09C 1/407* (2013.01); *C09D 5/22* (2013.01); *C09D 5/36* (2013.01); *C09D 7/1225* (2013.01); *C09D 7/1291* (2013.01); *A61K 2800/621* (2013.01); *B05D 5/06* (2013.01); *B05D 7/14* (2013.01); *C01P 2004/20* (2013.01); *C01P 2004/51* (2013.01); *C01P 2004/61* (2013.01); *C01P 2006/12* (2013.01); *C01P 2006/60* (2013.01); *C01P 2006/62* (2013.01); *C01P 2006/64* (2013.01); *C01P 2006/65* (2013.01); *C09C 2200/102* (2013.01); *C09C 2200/1004* (2013.01); *C09C 2200/301* (2013.01); *C09C 2200/308* (2013.01); *Y10T 428/258* (2015.01)

(56) References Cited

U.S. PATENT DOCUMENTS

| | | |
|---|---|---|
| 2004/0166316 A1 | 8/2004 | Noguchi |
| 2005/0176850 A1 | 8/2005 | Schmidt et al. |
| 2007/0032573 A1 | 2/2007 | Yanagase et al. |
| 2008/0035017 A1 | 2/2008 | Chung |
| 2009/0274735 A1 | 11/2009 | Wakamiya |
| 2010/0047300 A1 * | 2/2010 | Kaupp ............... A61K 8/25 424/401 |
| 2010/0083872 A1 | 4/2010 | Kitamura et al. |
| 2010/0116169 A1 | 5/2010 | Kaupp et al. |
| 2010/0129412 A1 * | 5/2010 | Kitamura ............ A61K 8/19 424/401 |
| 2011/0064951 A1 | 3/2011 | Fujiwara et al. |
| 2011/0151261 A1 | 6/2011 | Fujiwara et al. |

FOREIGN PATENT DOCUMENTS

| | | | |
|---|---|---|---|
| CN | 101404975 | 4/2009 | |
| CN | 102026929 | 4/2011 | |
| EP | 1 564 261 | 8/2005 | |
| EP | 2 008 641 | 12/2008 | |
| JP | 6-240172 | 8/1994 | |
| JP | 10-279828 | 10/1998 | |
| JP | 2002-509561 | 3/2002 | |
| JP | 2002-155241 | 5/2002 | |
| JP | 2003-055573 | 2/2003 | |
| JP | 2004-168940 | 6/2004 | |
| JP | EP 1524305 A2 * | 4/2005 | ............. C08L 53/00 |
| JP | 2005-314649 | 11/2005 | |
| JP | 2008-045097 | 2/2006 | |
| JP | 2010-031166 | 2/2010 | |
| JP | 2010-538096 | 12/2010 | |
| WO | 97/46624 | 12/1997 | |
| WO | 03/006558 | 1/2003 | |
| WO | 2005/028566 | 3/2005 | |
| WO | 2007/114442 | 10/2007 | |
| WO | 2008/136471 | 11/2008 | |
| WO | 2009/154064 | 12/2009 | |
| WO | 2010/024283 | 3/2010 | |

OTHER PUBLICATIONS

Office Action issued in corresponding Japan Application No. 2013-548321, Jun. 16, 2016, 2 pages.
Extended European Search Report issued for corresponding European patent application No. 12856041.4, Mar. 17, 2017, 4 pages.
European Office Action issued for corresponding European patent application No. 12856041.4, Mar. 17, 2017, 4 pages.

* cited by examiner

PHOTOLUMINESCENT PIGMENT, AND PHOTOLUMINESCENT PAINT COMPOSITION AND AUTOMOBILE OUTER PANEL COATING MATERIAL CONTAINING SAME

TECHNICAL FIELD

The present invention relates to a bright pigment, a bright paint composition and an automobile outer panel coating material containing the bright pigment, and a method for producing a bright pigment.

BACKGROUND ART

Conventionally, as a bright pigment such as a pearlescent pigment, a pigment in which each of flaky particles such as mica flakes, synthetic mica flakes, silica flakes, alumina flakes, glass flakes, or graphite flakes is covered with a covering layer containing a metal oxide such as titanium dioxide or iron oxide, iron oxide particles containing α-iron oxide crystals as a main component, and the like have been known. Those pearlescent pigments glitter by reflecting incident light from the outside on surfaces thereof, and impart unique surface appearances that are varying and have beautiful effects to a coating surface when blended with a paint, to a drawn line or a printing surface when blended with ink, or to a surface of a resin molding when blended with a resin composition, together with color tones of various substrate surfaces thereof.

In order to enhance beauty, the pearlescent pigments have been used widely for various applications such as an automobile, a motorcycle, office automation (OA) equipment, a mobile phone, a household electric appliance, various printed matters, and writing instruments.

Titanium dioxide has three kinds of crystal forms including anatase, brookite, and rutile. Of those, anatase and rutile titanium dioxides have been produced industrially. Anatase titanium dioxide has a high photocatalytic activity, and hence accelerates the degradation of components and discoloration of a resin composition portion and a paint composition. On the other hand, rutile titanium dioxide has a photocatalytic activity that is about one tenth of that of anatase titanium dioxide and is suitable for being blended as a pigment with a paint composition or a resin composition.

Patent document 1 discloses a bright pigment including flaky particles and a metal oxide layer covering at least a part of the surface of each flaky particle. The flaky particles are formed of a material having a particle diameter corresponding to a 99% volume-cumulative particle diameter from a small particle diameter side, in a particle size distribution, of 48 μm or less and having a maximum particle size of 62 μm or less and a refractive index of 1.4 to 1.8. In the thickness distribution of the flaky particles, the frequency of the occurrence of particles having a thickness ranging from 0.8 μm to 1.9 μm is 90% by volume or more, or the frequency of the occurrence of particles having a thickness ranging from 0.01 μm to 0.35 μm is 90% by volume or more. The problems to be solved by the invention described in Patent document 1 are to prevent particles of various colors from being mixed to glitter due to the difference in thickness of respective flaky particles and to achieve both a satisfactory filtration property and a satisfactory coating film finishing property.

PRIOR ART DOCUMENT

Patent document

Patent document 1: WO2008/136471

DISCLOSURE OF INVENTION

Problem to be Solved by the Invention

However, in particular, in the automobile industry, there is a demand for marketing a bright pigment and a bright paint composition containing the bright pigment that is more excellent in a single color development property and that is capable of forming a coating material realizing a more satisfactory coating film finishing property. It should be noted that being excellent in "a single color development property" as used herein means that color development with 0th-order interference caused by a relationship between the thickness of a flaky particle and the refractive index thereof does not occur or color development with 0th-order interference hardly occurs.

The present invention provides a bright pigment and a bright paint composition that are excellent in a single color development property and that are capable of forming a coating material which exhibits a satisfactory coating film finishing property; an automobile outer panel coating material formed through use of the bright pigment and the bright paint composition; and a method for producing a bright pigment.

Means for Solving Problem

A bright pigment of the present invention includes a flaky particle and a metal oxide layer covering a surface of the flaky particle. The bright pigment has a particle diameter corresponding to a 90% volume-cumulative particle diameter from a small particle diameter side, in a particle size distribution, of 55 μm or less. The flaky particle is formed of a material having a refractive index of 1.4 to 1.8. The flaky particle has an average thickness of 0.35 μm to 0.55 μm and does not substantially contain a flaky particle having a thickness of 0.15 μm or less.

A bright paint composition of the present invention includes the bright pigment of the present invention.

An automobile outer panel coating material of the present invention includes a metallic base layer containing 0.1 to 30% by mass of the bright pigment of the present invention.

A method for producing a bright pigment of the present invention is a production method for a bright pigment containing a flaky particle and a metal oxide layer covering a surface of the flaky particle.

The method includes:

a step (step 1) of adding an aqueous solution of a metal compound to a slurry for forming a metal oxide layer containing the flaky particle and acid to deposit a hydrate of an oxide of a metal derived from the metal compound on the surface of the flaky particle, thereby covering the flaky particle with a metal oxide hydrate layer containing the hydrate of the oxide of the metal; and a step (step 2) of washing and drying the flaky particle covered with the metal oxide hydrate layer, and baking the resultant flaky particle covered with the metal oxide hydrate layer to form the metal oxide hydrate layer into a metal oxide layer.

The flaky particle is formed of a material having a refractive index of 1.4 to 1.8.

The flaky particle has an average thickness of 0.35 μm to 0.55 μm and does not substantially contain a flaky particle having a thickness of 0.15 μm or less.

The bright pigment has a particle diameter corresponding to a 90% volume-cumulative particle diameter from a small particle diameter side, in a particle size distribution, of 55 μm or less.

Effects of the Invention

The present invention does not substantially contain flaky particles having a thickness of 0.15 μm or less, and hence can provide a bright pigment and a bright paint composition that are excellent in a single color development property and that are capable of forming a coating material which exhibits a satisfactory coating film finishing property; an automobile outer panel coating material formed through use of the bright pigment and the bright paint composition; and a method for producing the bright pigment.

DESCRIPTION OF THE INVENTION

Figure 1:
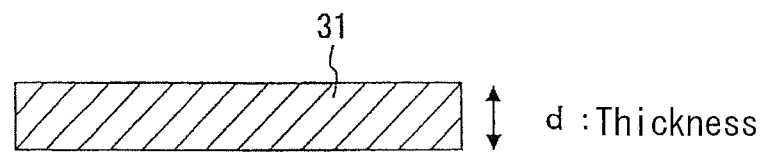
FIG. 1 is a schematic view showing thickness of a flaky particle.

In the present invention, a bright pigment has a particle diameter corresponding to a 90% volume-cumulative particle diameter from a small particle diameter side, in a particle size distribution, of 55 μm or less. Flaky particles are formed of a material having a refractive index of 1.4 to 1.8. The flaky particles have an average thickness of 0.35 to 0.55 μm and substantially do not contain flaky particles having a thickness of 0.15 μm or less. Therefore, a satisfactory coating film finishing property is obtained, and color development with 0th-order interference caused by a relationship between the thickness of a flaky particle (base) and the refractive index thereof does not occur or color development with 0th-order interference hardly occurs. Accordingly, the present invention can provide a bright pigment capable of forming a coating material having an excellent single color development property and a satisfactory film coating finishing property; a bright paint composition containing the bright pigment, and an automobile outer panel coating material.

In a preferred embodiment of the present invention, the thickness of a metal oxide layer covering each flaky particle and containing a metal oxide having a high refractive index is made uniform for respective flaky particles. That is, a bright pigment having high brightness is obtained by suppressing the variation in thickness of a metal oxide layer. The degree of variation in thickness of a metal oxide layer can be evaluated based on a thickness variation coefficient of a metal oxide described below. As a value of a thickness variation coefficient is smaller, the variation in thickness of a metal oxide layer is smaller. The thickness variation coefficient is preferably 20% or less, more preferably 10% or less.

Thickness variation coefficient of metal oxide layer=
(Standard deviation of thickness of metal oxide layer/average thickness of metal oxide layer)

The specific surface area of a conventional bright pigment containing a metal oxide layer made of rutile titanium dioxide or iron oxide is high (10 $m^2$/g or more), and a refractive index is not increased due to the insufficient density of crystal particles of rutile titanium dioxide or iron oxide, with the result that a bright pigment having high brightness has not been obtained. Further, in the case of using a bright pigment, in which flaky particles are covered with a metal oxide layer made of rutile titanium dioxide or iron oxide, for an automobile outer panel paint, the weather resistance has not been sufficient. Therefore, in the case where the flaky particles are made of silica, the specific surface area of a bright pigment has been lowered by filling pores of silica by covering silica with a metal oxide layer made of rutile titanium dioxide or iron oxide, and further, the metal oxide layer has been covered with a protective covering film containing materials absorbing ultraviolet light such as cerium, aluminum, or zirconium. However, when the metal oxide layer is covered with the protective covering film, there also has been a disadvantage in that a refractive index decreases and high brightness is not obtained.

In order to solve the above-mentioned problems, as an example of an interference pigment having high brightness, there has been proposed an interference pigment whose refractive index and surface smoothness are enhanced by allowing the metal oxide layer containing titanium oxide covering flaky particles to contain Ca and Mg (see, for example, JP 10-279828 A).

Further, there has been proposed an interference pigment in which the surface of each flaky particle is covered with a multi-layered covering layer including at least two metal oxide layers containing at least one kind of a metal selected from the group consisting of Ce, Sn, Ti, Fe, Zn, and Zr (see, for example, JP 2004-168940 A). However, the specific surface area of the interference pigment described in JP 2004-168940 A is about 3.0 to 10 $m^2$/g, and hence it still could not be said that the brightness and the weather resistance are sufficient for use in an automobile outer panel paint.

In a preferred embodiment of the present invention, each flaky particle is covered with a metal oxide layer having high density with the number of pores being small, and hence a bright pigment having high brightness and weather resistance can be provided. Specifically, when flaky particles containing a sodium component (sodium compound) are used, a metal oxide layer containing a dense crystal phase having a small specific surface area is obtained by a liquid phase deposition method as described later, and therefore, a bright pigment having a high refractive index is obtained. Further, it is preferred that a metal oxide layer become dense because, in the case where a metal oxide is titanium dioxide or iron oxide, active points of a photocatalyst decrease in number, and the weather resistance of a bright pigment is enhanced.

The content of the sodium component in the flaky particles varies depending on the kind of the sodium component. In the case where the sodium component is $Na_2O$, the content of the sodium component is preferably 3% by mass or more and less than 9% by mass. It should be noted that the mass of the metal oxide layer is much smaller than that of the flaky particles, and the mass of the metal oxide layer in the bright pigment is negligible. The specific surface area of the bright pigment is preferably less than 3.0 m²/g from the viewpoint of increasing a refractive index to enhance brightness.

In a preferred embodiment of the present invention, when the bright pigment has a particle diameter corresponding to a 90% volume-cumulative particle diameter from a small particle diameter side, in a particle size distribution, of 35 to 50 μm, a bright pigment having a satisfactory filtration property is obtained. Therefore, a bright pigment is obtained, that is capable of obtaining an excellent single color development property, high brightness, a satisfactory filtration, and a satisfactory coating film finishing property with good valance, by a combination with the above-mentioned preferred embodiments.

Regarding a method for covering flaky particles with a metal oxide (forming a metal oxide layer), physical vapor deposition (PVD) and chemical vapor deposition (CVD) are known as a vapor phase method, and liquid phase deposition (LPD) and a hydrothermal treatment are known as a liquid phase method. Of those, the liquid phase deposition (LPD) is preferred because this method enables a hydrate of a metal oxide to be formed easily on the surfaces of the flaky particles without unevenness, allows the thickness of a metal oxide to be uniform easily, and is economical due to high productivity.

According to the liquid phase deposition method, a hydrate of a metal oxide is formed in a reaction solution of pH 0.9-1.2 containing hydrochloric acid, for example, in the case where the metal oxide is titanium dioxide, and a hydrate of a metal oxide is formed in a reaction solution of pH 2.0-3.5 containing hydrochloric acid, for example, in the case where the metal oxide is iron oxide. If the composition of flaky particles contains a sodium component (sodium compound such as $Na_2O$), sodium (Na) diffuses from inside of a flaky particle to a surface layer in the reaction solution, with the result that an electric double layer is formed at an interface between the flaky particle and the liquid. Then, the concentration of sodium on the surface of the flaky particle increases. In the case where a metal oxide is titanium dioxide, hydrolysis of titanium tetrachloride (metal compound) occurs, with the result that a layer substantially made of a hydrate of titanium dioxide is formed selectively on the surface of the flaky particle. In the case where a metal oxide is iron oxide, hydrolysis of iron chloride (metal compound) occurs, with the result that a layer substantially made of a hydrate of iron oxide is formed selectively on the surface of the flaky particle, in the same way as in titanium dioxide.

It should be noted that reduced titanium oxide is obtained by reducing titanium oxide in an atmosphere containing hydrogen at 400° C. to 600° C., and reduced iron oxide is obtained by reducing iron oxide in an atmosphere containing hydrogen at 400° C. to 600° C.

It is preferred that a zeta potential of the flaky particles be for example −20 mV to −10 mV in a reaction solution of pH 2 because a stable electric double layer can be formed. In order to realize a zeta potential of −20 mV to −10 mV, it is preferred that components of the flaky particles contain a sodium component. In the case where the sodium component is $Na_2O$, it is preferred that the content of the sodium component in the flaky particles be 3% by mass or more and less than 9% by mass. The reaction solution contains flaky particles, water, and an acid. As the acid, there may be given hydrochloric acid, nitric acid, or sulfuric acid, and hydrochloric acid is preferred from the viewpoint of rapidly depositing rutile hydrous titanium dioxide on the surfaces of the flaky particles.

The present invention further includes a color base layer being disposed on one principal plane side of a base material to be coated for an automobile outer panel and having L* of a CIE L*a*b* color system of 40 or more, a metallic base layer being disposed on the color base layer and containing 0.1 to 30% by mass of the bright pigment of the present invention, and a top clear layer disposed on the metallic base layer.

It should be noted that, in the present specification, the particle diameter of the flaky particles refers to a light scattering nominal diameter obtained by measuring the flaky particles by a laser diffraction/scattering method. For example according to "Saishin Funtai Bussei Zusetsu (Physical Properties of Powder Particles with Illustrations, Latest Version (3rd edition)" (issued by Yutaka KURATA, published by NGT Co., Jun. 30, 2004), the light scattering nominal diameter is defined as a diameter of a sphere exhibiting a scattering pattern closest to a light scattering pattern of a particle obtained by measurement and having the same refractive index as that of the particle.

Further, the particle size distribution is an index indicating which size (particle diameter) of particles are contained in which ratio in a group of particles to be measured, and in the present specification, the particle size distribution is measured by the laser diffraction/scattering method. The laser diffraction/scattering method is a method for determining a particle size distribution through use of scattered light obtained when particles are irradiated with light, and in the particle size distribution in the present specification, a volume is used as a reference of a particle amount. The maximum particle diameter refers to a particle diameter corresponding to a 100% volume-cumulative particle diameter in a particle size distribution.

Further, the thickness distribution refers to an index indicating which thickness of particles are contained in which ratio in a group of particles to be measured. In the present specification, the length of a portion denoted with "d" of a flaky particle 31 shown in FIG. 1 is measured as a thickness of a flaky particle. Specifically, a predetermined number (preferably 100 or more) flaky particles are extracted from a group of particles to be measured, and the thickness "d" of each particle is measured through use of an electron microscope, whereby a thickness distribution is obtained.

First, regarding the problems to be solved by the invention, the results obtained by the earnest study conducted by the inventor are described below.

(Interference Color Caused by Thickness of Flaky Particle)

As described above, it is an object of the present invention to prevent a phenomenon in which particles of various colors are mixed to glitter in a bright pigment. That particles of various colors are mixed is a phenomenon caused by the difference in interference color due to the thickness of flaky particles, which is described below. It should be noted that, in the present specification, the thickness of a flaky particle refers to the thickness of the portion denoted with "d" in FIG. 1. Herein, a bright pigment in which a metal oxide layer of titanium dioxide and/or iron oxide is provided on each surface of flaky particles is exemplified.

A bright pigment is formed by covering each flaky particle with a metal oxide layer of titanium dioxide and/or iron oxide. The bright pigment develops various colors as a whole due to the interference of reflected light, for example, when the thickness of a metal oxide layer having a high refractive index varies depending on a bright pigment, and there is unevenness in thickness in the bright pigment.

On the other hand, a flaky particle positioned in a metal oxide layer while being covered therewith also develops a color due to the interference in a predetermined thickness range in the same way as in the metal oxide layer.

When light enters a thin film layer such as a metal oxide layer, an optical path difference between light reflected from an interface which the light enters and light reflected from the other interface (optical path difference between reflected light from an upper surface of the thin film layer and reflected light from a lower surface thereof) is represented by the following expression (1).

$$2nd \times \cos \gamma \quad (1)$$

(n: refractive index of a thin film layer, d: thickness of a thin film layer (μm), γ: refraction angle of a thin film layer)

In the bright pigment of the present example, the refractive index of titanium dioxide and/or iron oxide used in the metal oxide layer is higher than that of each material used in the flaky particles. That is, in the case where a bright pigment composition containing a bright pigment is used, and a residue obtained by excluding the bright pigment from a coating film formed of the bright pigment composition is referred to as a medium layer, a relationship of refractive indices of (medium layer/metal oxide layer/flaky particle/metal oxide layer/medium layer) is as represented by the following Expression (2). Further, specific examples of a refractive index N of the medium, a refractive index $n_1$ of the metal oxide, and a refractive index $n_0$ of the flaky particle are also described below.

$$N \text{ (medium layer)} < n_1 \text{ (metal oxide layer)} > n_0 \text{ (flaky particle)} < n_1 \text{ (metal oxide layer)} > N \text{ (medium layer)} \quad (2)$$

Refractive index N of medium: acrylic resin (1.49)
Refractive index $n_1$ of metal oxide: rutile titanium dioxide (2.71)
  anatase titanium dioxide (2.52)
  iron oxide (3.01)
Refractive index $n_0$ of flaky particle: C glass (1.54)
  Silica (1.46)
  Alumina (1.76)
  Mica, synthetic mica (1.55 to 1.59)

In light reflected from the bright pigment of this example, the reflection from a boundary surface between the metal oxide layer ($n_1$) and the flaky particle ($n_0$) on the light incident side does not involve a change in phase. However, the reflection from a boundary surface between the flaky particle ($n_0$) and the metal oxide layer ($n_1$) on the side opposite to the light incident side involves a shift of a phase by π (rad), and hence, a light band condition under which the flaky particle and the metal oxide layer strengthen reflected light with each other is represented by the following Expression (3):

$$2n_0 d \times \cos \gamma = \frac{1}{2} \times \lambda \times (2m+1) \quad (3)$$

λ: wavelength of reflected light (μm), $n_0$: refractive index of flaky particle,
d: thickness of flaky particle (μm), m: order of interference (integers of 0, 1, 2, 3 . . . ),
γ: refraction angle of metal oxide layer It can be determined by Expression (3) in which color reflected light looks depending on the thickness of a flaky particle. In the case where the wavelength λ of visible light is defined to be 380 to 780 nm, and $n_0$ is defined to be 1.4 to 1.8, a 0th-order interference color appears in flaky particles having a thickness range of more than 0.05 μm and 0.15 μm or less, and it looks as if the flaky particles themselves are colored. Then, it was found that a single color development property can be enhanced by substantially not including particles having a thickness of 0.15 μm or less in a thickness distribution of the flaky particles.

(Influence of Thickness and Coarse Particles of Bright Pigment on Coating Film Finishing Property)

Roughly two requests are made with respect to an automobile outer panel coating material (coating). One request is to protect a coating lower portion (steel plate) from being corroded, and the other request is to achieve an attractive design property (vivid single color development property) as described above and smooth outer appearance quality with a high gloss like a mirror.

As terms for expressing the above-mentioned outer appearance quality, there may be given "Glossy", "Dull", "DOI: Distinctness of Image", "Orange Peel, and the like.

Further, the outer appearance quality is determined by the variation in light reflection caused by an uneven pattern of a coating surface and is recognized visually by a human. As a method for optically evaluating a light/dark pattern of a wavelength of a coating surface as by human eyes, Micro-Wave-Scan (manufactured by Paul N. Gardener Co., Inc.) has been known.

In the Micro-Wave-Scan, a point light source of a laser irradiates a coating sample surface with laser light at an angle tilted by 60° from a normal to the coating sample surface, and a detector measures reflected light at the same angle opposite with respect to the normal. The Micro-Wave-Scan can detect an optical profile of the coating sample surface by scanning the coating sample surface with the point light source of the laser that is moved over the coating sample surface, thereby measuring lightness/darkness of reflected light on a point basis at a predetermined interval. The detected optical profile is subjected to spectrum analysis through a frequency filter, and each structure of an underlying portion, an inside, and a surface of the coating can be analyzed. A characteristic spectrum of the Micro-Wave-Scan is as follows.

du: wavelength of 0.1 mm or less
  Wa: wavelength of 0.1 to 0.3 mm
  Wb: wavelength of 0.3 to 1 mm
  Wc: wavelength of 1 to 3 mm
  Wd: wavelength of 3 to 10 mm
  We: wavelength of 10 to 30 mm
  Sw: wavelength of 0.3 to 1.2 mm
  Lw: wavelength of 1.2 to 12 mm
  DOI: wavelength of 0.3 mm or less.

The inventor of the present invention found that the thickness and coarse particles of the bright pigment influence outer appearance characteristics such as "Dull" and "DOI: Distinctness of Image" of an automobile outer panel coating material including a metallic base layer. Specifically, it was found that, when the thickness of the bright pigment increases, intensities of characteristic spectrum such as du (wavelength: 0.1 mm or less), Wa (wavelength: 0.1 to 0.3 mm), Sw (wavelength: 0.3 to 1.2 mm), and DOI (wavelength: 0.3 mm or less) increase and the outer appearance characteristics such as "Dull" and "DOI: Distinctness of Image" are affected adversely.

Further, when the number of coarse particles in the bright pigment increases, intensities of the characteristics spectrum such as du (wavelength: 0.1 mm or less), Wa (wavelength: 0.1 to 0.3 mm), Sw (wavelength: 0.3 to 1.2 mm), and DOI (wavelength: 0.3 mm or less) increase and the outer appearance characteristics such as "Dull" and "DOI: Distinctness of Image" are affected adversely.

Based on the foregoing results, the inventor of the present invention proposes the bright pigment of the present invention as follows.

The bright pigment of the present invention includes flaky particles and a metal oxide layer covering at least a part of a surface of each flaky particle. The bright pigment has a particle diameter corresponding to a 90% volume-cumulative particle diameter from a small particle diameter side, in a particle size distribution, of 55 μm or less. Further, the flaky particles are formed of a material having a refractive index of 1.4 to 1.8. Further, the flaky particles have an average thickness of 0.35 to 0.55 μm and do not substantially contain flaky particles having a thickness of 0.15 μm or less.

(Flaky Particle)

The flaky particles have an average thickness of 0.35 μm to 0.55 μm, preferably 0.40 to 0.50 μm, more preferably 0.42 μm to 0.48 μm in a thickness distribution of the flaky particles and substantially do not include flaky particles having a thickness of 0.15 μm or less. Herein, not substantially including flaky particles having a thickness of 0.15 μm or less means that the proportion of flaky particles having a thickness of 0.15 μm or less is 1% or less, preferably 0.5% or less, more preferably 0% in terms of the number. According to the present application, in a subtitle <Thickness distribution of flaky particles> described later, when the thickness "d" (see FIG. 3) of each of any 100 flaky particles is measured with an electron microscope, it is found that the number of flaky particles having a thickness of 0.15 μm or less is, for example, one or less, this means that the proportion of flaky particles having a thickness of 0.15 μm or less is 1% or less in terms of the number.

The flaky particles are formed of a material having a refractive index of 1.4 to 1.8. It is preferred that the flaky particles be formed of an inorganic material, and it is preferred that the flaky particles be formed of one material selected from the group consisting of glass, silica, alumina, and mica for the reason of high transparency with respect to visible light. Although the material for the flaky particles is not specifically limited, it is more preferred to use flaky glass particles having high surface smoothness and high transparency. In this case, a bright pigment excellent in a single color development property can be provided by covering each flaky glass particle with a metal oxide layer containing titanium dioxide and/or iron oxide as main components.

It is preferred that the composition of the flaky particles contain a sodium component such as $Na_2O$ for the reason that a stable electric double layer is formed. The content of the sodium component is preferably 3% by mass or more and less than 11% by mass, more preferably 3% by mass or more and less than 9% by mass, still more preferably 5% by mass or more and less than 9% by mass, still further preferably 7% by mass of more and less than 9% by mass.

For enhancing a glittering appearance, in the particle size distribution, the particle diameter corresponding to a 90% volume-cumulative particle diameter from a small particle diameter side of the flaky particles is 35 to 55 μm, preferably 35 to 50 μm, more preferably 40 to 50 μm, and still more preferably 42 to 48 μm. It should be noted that the thickness of a covering film such as a metal oxide layer is negligibly small with respect to the particle diameter of a flaky particle.

From the viewpoint of enhancing a filtration property, in the particle size distribution, the particle diameter corresponding to a 90% volume-cumulative particle diameter from a small particle diameter side of the flaky particles is preferably 50 μm or less and the maximum particle diameter of the flaky particles is preferably 105 μm or less. In the particle size distribution, the particle diameter corresponding to a 90% volume-cumulative particle diameter from a small particle diameter side of the flaky particles is more preferably 48 μm or less and the maximum particle diameter of the flaky particles is more preferably 88 μm or less. In the particle size distribution, the particle diameter corresponding to a 90% volume-cumulative particle diameter from a small particle diameter side of the flaky particles is still more preferably 46 μm or less and the maximum particle diameter of the flaky particles is still more preferably 74 μm or less.

From the viewpoint of enhancing a coating film finishing property, in the thickness distribution, the frequency of the occurrence of flaky particles having a thickness ranging from 0.25 μm to 0.65 μm is preferably 90% or more, more preferably 95% or more in terms of the number. According to the present application, in the subtitle <Thickness distribution of flaky particles> described later, when the thickness "d" (see FIG. 3) of each of any 100 flaky particles is measured with an electron microscope and it is found that the number of flaky particles having a thickness of 0.25 μm to 0.65 μm is 90 or more, this means that the frequency of the occurrence of flaky particles having a thickness ranging from 0.25 μm to 0.65 μm is 90% or more in terms of the number.

Figure 2:
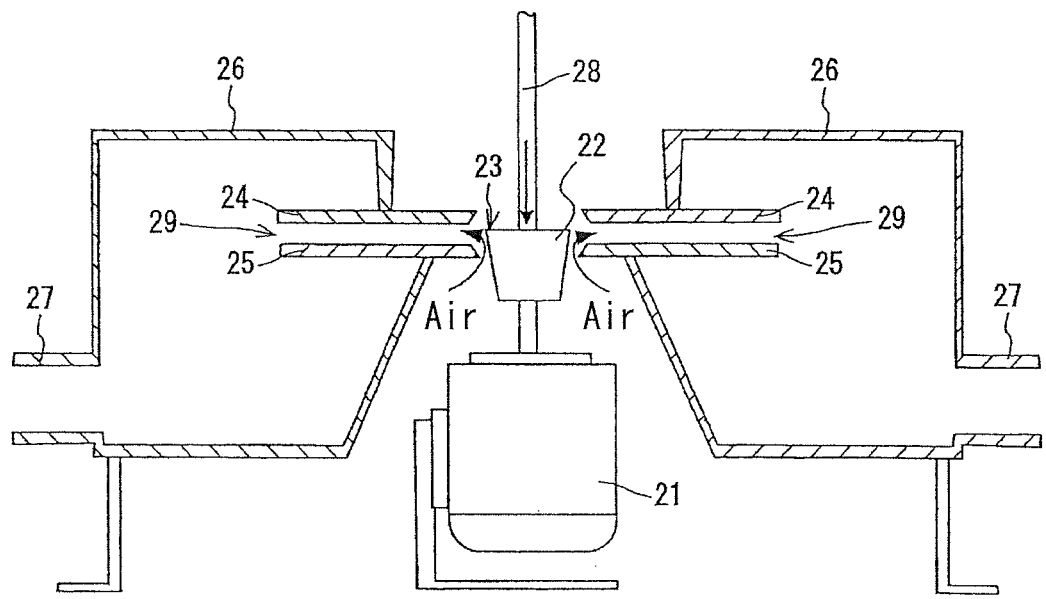
FIG. 2 is a partial sectional view schematically showing an example of an apparatus for producing a flaky particle forming a bright pigment of the present invention.

The flaky glass particles may be produced, for example, by producing a thin glass film through use of a flow of molten glass caused by a centrifugal force and crushing the glass film. FIG. 2 shows an example of an apparatus for producing flaky glass particles through use of a flow of molten glass. The apparatus includes a tapered cup 22 attached to a variable-speed electric motor 21, and a rim 23 of the cup 22 is positioned between two annular plates 24, 25. An upper plate 24 is provided so as to move vertically, and the distance between the plates 24, 25 can be regulated. The plates 24, 25 are attached inside a cyclone-type vacuum chamber 26, and the chamber 26 is connected to a cyclone collection/separation/vacuum pump (not shown) via an outlet connection 27. The cup 22 is rotated at a predetermined speed, and molten glass 28 is poured into the cap 22 from above. The molten glass in the cup 22 is sent outside beyond the rim 23 due to the centrifugal force. The pressure inside the chamber 26 is lowered by operating the cyclone collection-separation-vacuum pump, and air enters the chamber 26 through a region 29 between the plates 24, 25. The air having entered the chamber 26 quenches the molten glass sent outside beyond the rim 23 of the cup 22. Further, an airflow flowing between the plates 24, 25 also has a function of holding the molten glass so that the molten glass sent beyond the rim 23 of the cup 22 and positioned between the plates 24, 25 does not come into contact with the surfaces of the plates 24, 25. The airflow between the plates 24, 25 cools the molten glass between the plates 24, 25 until the molten glass becomes a solid. The glass positioned between the plates 24, 25 is pulled out in a radial direction due to the friction with the airflow and crushed into small flake-shaped glass particles while being kept in a plate shape by the airflow. The flaky glass particles thus obtained are collected in the chamber 26 and sent to a cyclone collection/filtration section (not shown) through the outlet connection 27.

In the case of producing flaky glass particles through use of the apparatus, the thickness of the flaky glass particles can be regulated by regulating the distance between the plates 24, 25, the speed of the airflow between the plates 24, 25, and the like.

A preferred example of a composition of the flaky particles is described below.

TABLE 1

Composition of flaky synthetic mica particles

|  | Reference example Fluorine gold mica $KMg_3(AlSi_3O_{10})F_2$ | Reference example Potassium tetrasilicon mica $KMg_{2.5}(Si_4O_{10})F_2$ | Example of present invention Sodium tetrasilicon mica $NaMg_{2.5}(Si_4O_{10})F_2$ |
|---|---|---|---|
| $SiO_2$ | 40-50 | 53-65 | 55-65 |
| $Al_2O_3$ | 6-15 | — | — |
| MgO | 25-35 | 20-28 | 21-29 |
| $Na_2O$ | — | — | 4-9 |
| $K_2O$ | 5-10 | 7-13 | — |
| F | 5-13 | 7-14 | 6-15 |

(Unit: % by mass)

TABLE 2

Composition of flaky alumina particles

|  | Example of present invention | Reference example | Reference example |
|---|---|---|---|
| $Al_2O_3$ | 92.8 | 97.9 | 78.5 |
| $Na_2O$ | 4.2 | 0.1 | 1.3 |
| $K_2O$ | 2 | — | 17.4 |
| $TiO_2$ | — | 0.8 | 1 |
| $P_2O_5$ | 1 | 1.2 | 1.8 |

(Unit: % by mass)

TABLE 3

Composition of flaky glass particles

|  | Example of present invention | A glass | C glass | ECR glass | WO2006/068255 |
|---|---|---|---|---|---|
| $SiO_2$ | 59-69 | 70-73 | 65-70 | 55-60 | 60-65 |
| $Al_2O_3$ | 2-12 | 1.0-1.8 | 1-7 | 9-13 | 8-12 |
| CaO | 5-18 | 7-12 | 4-11 | 15-25 | 20-24 |
| MgO | 0-5 | 1.0-4.5 | 0-5 | 1-5 | 1-5 |
| $B_2O_3$ | 0-7 | — | 0-8 | — | — |
| $Na_2O$ | 3-9 | 10-13 | 9-14 | 0-2 | 0-2 |
| $K_2O$ | 0-1 | 0-3 | 0-3 | 0-1 | 0-1 |
| ZnO | 0-2 | — | 0-6 | 1-5 | — |
| $TiO_2$ | — | — | — | 1-5 | 0-5 |
| FeO/$Fe_2O_3$ | — | 0-0.2 | — | — | — |

(Unit: % by mass)

(Classification Method)

In the present invention, the particle size of flaky particles can be adjusted by, for example, sieve classification. For example, a dry-type vibrating sieving machine can be used for sieve classification. It is appropriate that the mesh size of a sieve to be used is selected appropriately depending on the particle size of the flaky particles before sieving or the target particle diameter of the flaky particles.

Further, a classification method other than the sieve classification may be used in order to remove fine powder and coarse powder.

In the case of dry classification, an airflow classifier such as a gravitational classifier, an inertial classifier, and a centrifugal classifier can be used for removing coarse powder. As a gravitational classifier, horizontal flow-type, vertical flow-type, and inclined flow-type classifiers, for example, can be used. As an inertial classifier, linear-type, curving-type, and louver-type classifiers, an Elbow-Jet, and a Variable Impactor, for example, can be used. As a centrifugal classifier using air vortex, cyclone-type, Vantongeren-type, and classiclone-type classifiers, a Dispersion Separator, and a Microplex can be used. As a centrifugal classifier using mechanical rotation, a Micron Separator, a Turboplex, an Acucut, a Turbo Classifier, and the like can be used.

In the case of wet classification, an airflow classifier such as a gravitational classifier and a centrifugal classifier can be used. As a gravitational classifier using gravity settling tanks, a settling tank, a deposition cone, a Spitzkasten, and a Hydroseparator can be used. As a gravitational classifier using mechanical rotation, a drag chain classifier, a rake classifier, a ball classifier, a spiral classifier and the like can be used. As a hydraulic classifier, a "doruko" sizer, a Valenwald sizer, a syphon sizer, a hydroscillator, and the like can be used. As a centrifugal classifier, hydrocyclone and centrifugal classifiers (disk-type and decanter-type) and the like can be used.

(Metal Oxide Layer)

A specific example of the metal oxide layer is described below.

It is preferred that a metal oxide contained in a metal oxide layer covering a flaky particle be at least one metal oxide selected from the group consisting of titanium dioxide ($TiO_2$), reduced titanium oxide ($TiO_{2-x}$), iron oxide ($Fe_2O_3$), and reduced iron oxide ($Fe_3O_4$) for the reason that a metal oxide layer having a high refractive index is likely to be formed.

Hereinafter, a metal oxide layer is described in detail by exemplifying titanium dioxide and iron oxide.

<Titanium Dioxide Layer>

As an example of the metal oxide layer covering each flaky particle, there is given a titanium dioxide layer. It is appropriate that the titanium dioxide layer covering each flaky particle is substantially composed of rutile titanium dioxide. When rutile titanium dioxide is used as a metal oxide, a bright pigment having high brightness is obtained because the metal oxide contains dense crystals having a small specific surface area and has high density, that is, a metal oxide layer has a high refractive index. Herein, the term "substantially" means that the amount of components other than titanium dioxide in the metal oxide layer is 0.1% by mass or less, preferably 0.01% by mass or less. Examples of the components other than titanium dioxide include $SnO_2$ and $Na_2O$.

Titanium dioxide has three kinds of crystal forms such as anatase, brookite, and rutile. Of those, anatase and rutile titanium dioxides have been produced industrially. Anatase titanium dioxide has a high photocatalytic activity, and hence accelerates the degradation of components and discoloration of a resin composition and a paint composition. On the other hand, rutile titanium dioxide has a photocatalytic activity that is about one tenth of that of anatase titanium dioxide and is suitable for being used as a pigment in a paint composition or a resin composition. Further, rutile titanium dioxide has a refractive index higher than that of anatase titanium dioxide and can easily form a dense and uniform covering film, and hence enhances a color development property due to the interference of light. As a method for producing a rutile titanium dioxide layer, there can be illustrated a method for depositing a hydrate of rutile titanium dioxide from a titanium-containing solution by a neutralization reaction under conditions of a temperature of 55° C. to 85° C. and a pH of 1.3 or less, preferably 0.9 to 1.2, as disclosed by JP 2001-31421 A. According to this method, heating for crystal form transformation is not basically required, and rutile titanium dioxide also can be easily fixed on a base (flaky particle) having low heat resistance. The thickness of a rutile titanium dioxide layer is preferably 20 nm to 350 nm, more preferably 30 nm to 300 nm, still more preferably 40 nm to 250 nm for the reason that the brightness by light reflection and an optical path difference sufficient for interference are obtained.

<Iron Oxide Layer>

As another example of the metal oxide layer covering each flaky particle, there is given an iron oxide layer. Iron oxide has a low photocatalytic activity that is about one tenth of that of anatase titanium dioxide in the same manner as rutile titanium dioxide and is suitable for being used as a pigment in a paint or a resin composition. The use of iron oxide can realize coloration of chromatic colors developed by absorption of light by iron oxide and colors (bronze color, orange color, red color) developed by interference of light, which are overlapped with each other. As iron oxide covering a flaky particle, a trivalent iron oxide, or a mixture of a bivalent iron oxide and a trivalent iron oxide can be used. It is appropriate that the iron oxide layer covering each flaky particle is substantially formed of the above-mentioned iron oxide. Herein, the term "substantially" means that the amount of components other than iron oxide in the metal oxide layer is 0.1% by mass or less, preferably 0.01% by mass or less. Examples of the components other than iron oxide include $SnO_2$ and $Na_2O$. As a method for producing an iron oxide layer, there can be illustrated a method for depositing a hydrate of iron oxide from an iron-containing solution by a neutralization reaction under conditions of a temperature of 50° C. to 80° C. and a pH of 2 to 4, preferably 2.0 to 3.5, as disclosed by JP 2005-187782 A. The thickness of an iron oxide layer is preferably 20 nm to 350 nm, more preferably 30 nm to 300 nm, still more preferably 40 nm to 250 nm for the reason that the brightness by light reflection and an optical path difference sufficient for interference are obtained.

In order to obtain a bright pigment having high brightness, it is important that the thickness of a metal oxide layer containing titanium dioxide, iron oxide, or the like covering each flaky particle as a main component is made uniform for respective flaky particles. When the thickness varies depending on the flaky particle, brightness is degraded. In the present invention, the thickness variation coefficient (standard deviation of thickness of metal oxide layer/average thickness of metal oxide layer) of the metal oxide layer is preferably 20% or less, more preferably 10% or less. still more preferably 8% or less from the viewpoint of enhancing a single color development property and brightness.

As described above, a liquid phase deposition (LPD) method is preferred as the method for forming a metal oxide layer.

In order to make uniform the thickness of a metal oxide layer containing rutile titanium dioxide, iron oxide, or the like serving as a high refractive index material as a main component, it is desired that the zeta potential of the flaky particles be set to be a negative potential. Rutile titanium oxide can be deposited by adjusting the concentration of chlorine in a reaction solution containing an acid such as hydrochloric acid. It is preferred that the pH of a reaction solution be lower than an isoelectric point of a metal oxide. The isoelectric point of rutile titanium oxide is pH 4.5, and that of iron oxide is 9.5.

According to the liquid phase deposition method, in the case where a metal oxide is titanium dioxide, it is preferred that a hydrate of a metal oxide be formed by soaking flaky particles in a reaction solution containing an acid such as hydrochloric acid preferably having a pH of 0.9 to 1.2, and in the case where a metal oxide is iron oxide, it is preferred that a hydrate of a metal oxide be formed by soaking flaky particles in a reaction solution containing an acid such as hydrochloric acid preferably having a pH of 2.0 to 4.0. It is more preferred that the composition of the flaky particles contain a sodium component for the following reason.

In a reaction solution, sodium diffuses from an inside of a flaky particle to a surface layer, and an electric double layer is formed at an interface between the flaky particle and the reaction solution. Then, the concentration of sodium on the surface of the flaky particle increases. In the case where a metal oxide is titanium dioxide, hydrolysis of titanium tetrachloride (metal compound) occurs, with the result that a layer substantially made of a hydrate of titanium dioxide is formed selectively on the surface of the flaky particle. In the case where a metal oxide is iron oxide, hydrolysis of iron chloride (metal compound) occurs, with the result that a metal oxide layer substantially made of a hydrate of iron oxide is formed selectively on the surface of the flaky particle.

It is preferred that a zeta potential of the flaky particles be for example −20 mV to −10 mV in a reaction solution of pH 2 because a stable electric double layer can be formed. It is preferred that the zeta potential of the flaky particles used for producing a bright pigment in a hydrochloric acid aqueous solution of pH2 be −20 mV to −10 mV because a stable electric double layer can be formed. In order to realize a zeta potential of −20 mV to −10 mV, it is preferred that components of the flaky particles contain a sodium component (for example, $Na_2O$), and the content of the sodium component in the flaky particles is preferably 3% by mass or more and less than 9% by mass, more preferably 5% by mass or more and less than 9% by mass. In other words, the concentration of Na in the flaky particles is preferably 3% by mass or more and less than 9% by mass, more preferably 5% by mass or more and less than 9% by mass in terms of the total mass of $Na_2O$.

Anatase titanium oxide can be transformed into a rutile crystal phase at high temperature (for example, 800° C. or more) in the presence of a crystal transformation catalyst such as tin oxide. However, there has been a disadvantage that, although anatase titanium oxide can be transformed into a rutile crystal phase, crystal grains are enlarged to lower the density of a metal oxide layer, with the result that the refractive index of a bright pigment decreases.

According to the liquid phase deposition method, in order to obtain a rutile crystal phase at a time when a hydrate of titanium dioxide is deposited on the surface of a flaky particle and the surface of the flaky particle is substantially covered with the hydrate of titanium dioxide, titanium tetrachloride (metal compound) whose anionic species ionic radius is small, containing chlorine, is preferred as a raw material derived from titanium, because the ionic radius of chlorine ions is close to the ionic radius of oxygen ions, and a slurry in which flaky particles are dispersed in an aqueous solution of hydrochloric acid is preferred as a slurry for forming a metal oxide layer. The pH of a reaction solution at 60° C. to 85° C. is preferably 1.3 or less, more preferably 0.9 to 1.2.

On the other hand, in order to substantially form a hydrate of iron oxide on the surface of a flaky particle similarly by the liquid phase deposition method, the pH of a reaction solution at 50° C. to 80° C. is preferably 2.0 to 4.0, more preferably 2.5 to 3.5

Thus, in order to uniform the thickness of a metal oxide layer covering a flaky particle, it is necessary to create conditions under which a hydrate of a metal oxide is deposited easily depending on the kind of the metal oxide and the material for the flaky particle.

In the present invention, in an acidic slurry for forming a metal oxide layer and reaction solution containing chlorine ions, a sodium component contained in flaky particles as an oxide of sodium diffuses from an inside of each flaky particle to the surface thereof, with the result that an electric double layer is formed at an interface between the flaky particle and the liquid. The zeta surface potential of each flaky particle becomes negative, and hydrolysis of titanium tetrachloride (metal compound) occurs in the vicinity of the surface of the flaky particle, and a hydrate of rutile titanium dioxide is deposited selectively on the surface of the flaky particle. The flaky particles each covered with a hydrate layer of rutile titanium dioxide are subjected to washing, drying, and baking to become a bright pigment in which each of the flaky particles is covered with a metal oxide layer containing rutile titanium dioxide as a main component. The surface of the flaky particle is covered with a metal oxide layer that is densely filled with small titanium dioxide particles. In the foregoing reaction system, the covering speed of a hydrate of rutile titanium dioxide proceeds quantitatively, and the occurrence of thickness unevenness of a metal oxide layer is suppressed, and the occurrence of thickness unevenness of metal oxide layers among flaky particles is also suppressed. It should be noted that the "metal oxide layer containing rutile titanium dioxide as a main component" means that a main component forming a metal oxide layer is rutile titanium dioxide, and that a metal oxide layer is substantially formed of rutile titanium dioxide.

Further, in the case where sodium is taken in a crystal phase, the dehydration and condensation reaction of rutile titanium dioxide is accelerated, and hence a metal oxide layer substantially formed of rutile titanium oxide having a small number of pores and high density is obtained. Further, the crystallization degree is enhanced by baking at low temperature (600° C. or less), and titanium dioxide particles do not become enlarged. In the thus obtained metal oxide layer containing rutile titanium dioxide as a main component, covering the surface of a flaky particle, dense crystals having a small specific surface area are obtained, and hence a bright pigment having high density of the metal oxide layer, that is, a high refractive index and having high brightness is obtained.

Further, the covering thickness of rutile titanium dioxide is made uniform for respective flaky particles, and hence the uniformity of interference light is increased and a bright pigment having high brightness is obtained.

Therefore, a preferred example of the method for producing a bright pigment of the present invention includes a deposition step (first step) of adding tin as needed to a slurry liquid containing flaky particles, hydrochloric acid, and water to obtain a slurry for forming a metal oxide layer, adding an aqueous solution of a metal compound to the slurry for forming a metal oxide layer, and depositing a hydrate of an oxide of a metal derived from the metal compound on a surface of each of the flaky particles; and a step (second step) of, after the deposition step, collecting the flaky particles with the hydrate of the oxide of the metal deposited thereon from the slurry for forming a metal oxide layer, subjecting the flaky particles each covered with a metal oxide hydrate layer to washing with water, drying, and baking, thereby forming a bright pigment containing the flaky particles and a metal oxide layer covering each of the flaky particles.

In the above-mentioned production method, the pH of the slurry liquid before the addition of tin is preferably 1.5 to 2.0 for the reason that each flaky particle is covered with tin oxide uniformly. In the case where a metal oxide is titanium dioxide, the temperature of the slurry for forming a metal oxide layer to which the aqueous solution of the metal compound is being added is kept at preferably 60° C. to 85° C., more preferably 70° C. to 80° C. The drying temperature is preferably 150° C. to 250° C. The baking temperature is preferably 400° C. to 700° C., more preferably 550° C. to 650° C. from the viewpoint of enhancing the crystallization degree of a metal oxide and preventing the enlargement of crystals. It should be noted that the drying temperature or the baking temperature is respectively atmospheric temperature in a drier or a baking furnace, and respectively can be checked through a temperature display section of the drier or the baking furnace.

In the first step, in the case where the metal oxide is at least one selected from titanium dioxide and reduced titanium oxide, the aqueous solution of the metal compound is added to the slurry for forming a metal oxide layer while keeping the pH of a mixture of the slurry for forming a metal oxide layer and the aqueous solution of the metal compound preferably at 0.9 to 1.2 with a basic aqueous solution. Further, in the first step, in the case where the metal oxide is at least one selected from iron oxide and reduced iron oxide, the aqueous solution of the metal compound is added to the slurry for forming a metal oxide layer while keeping the pH of a mixture of the slurry for forming a metal oxide layer and the aqueous solution of the metal compound preferably at 2.0 to 3.5 with a basic aqueous solution.

As the basic aqueous solution, sodium hydroxide, lithium hydroxide, potassium hydroxide, ammonia, or the like can be used.

(Other Covering Layer)

In automobiles or motorcycles used outdoors, pigments to be used therein are required to have high weather resistance. This is because exposure to ultraviolet light accelerates the degradation or discoloration of a coating film, due to the photocatalytic activity of titanium dioxide and/or iron oxide contained in the pigment. For the purpose of obtaining high weather resistance, it is preferred that the bright pigment further be covered with a hydroxide or a hydrated oxide of at least one element selected from the group consisting of lanthanum, cerium and aluminum. Further, in order to improve the adhesion to a coating film matrix resin (described later) in addition to the above-described weather resistance, it is preferred that the bright pigment be provided with a surface treatment layer as the outermost layer using an organic compound containing an oxazoline ring and/or a silane coupling agent.

<Hydroxide or Hydrated Oxide of Cerium>

A hydroxide or hydrated oxide of cerium can be deposited on particles (flaky particles covered with titanium dioxide and/or iron oxide) by reacting a water-soluble cerium compound with acid or alkali. Examples of the acidic cerium compound to be used include mineral acid salts such as cerium sulfate, cerium chloride, and cerium nitrate. The acidic cerium compound to be used can deposit a hydroxide or hydrated oxide of cerium by reacting with alkali such as an alkali metal hydroxide. Instead of the acidic cerium compound, an alkaline cerium salt such as ammonium cerium sulfate or ammonium cerium nitrate can be used, which deposits a hydroxide or hydrated oxide of cerium by reacting with acid such as sulfuric acid. It is preferred to use cerium nitrate as a water-soluble cerium compound and to use a sodium hydroxide solution as alkali which is to react with it. The amount of the cerium compound may be in a common range of about 0.01% by mass to about 1.0% by mass in terms of the total mass of cerium, with respect to the titanium dioxide and/or iron oxide to be used for the metal oxide layer in the present embodiment. In other words, the cerium compound to be used for forming a hydroxide or a hydrated oxide of cerium may be in a common range of about 0.01 parts by mass to about 1.0 part by mass in terms of the total mass of cerium, when the mass of titanium dioxide and/or iron oxide contained in the metal oxide layer is assumed to be 100 parts by mass. More preferably, the cerium compound is added to an aqueous slurry in an amount of about 0.02% by mass to about 0.5% by mass with respect to the titanium dioxide and/or iron oxide. In other words, when the mass of titanium dioxide and/or iron oxide contained in a metal oxide layer is assumed to be 100 parts by mass, the cerium compound is contained in an aqueous slurry used for forming a hydroxide or hydrated oxide of cerium in an amount ranging from about 0.02 parts by mass to about 0.5 parts by mass in terms of the total mass of cerium. The acid or alkali to be used is added to the slurry in an amount sufficient to react with the cerium compound to cause deposition of the hydroxide or hydrated oxide of cerium on the particles.

<Hydroxide or Hydrated Oxide of Lanthanum>

A hydroxide or hydrated oxide of lanthanum can be deposited on the particles (the flaky particles covered with titanium dioxide and/or iron oxide) by reacting a water-soluble lanthanum compound with acid or alkali. Examples of the lanthanum compound to be used include mineral acid salts such as lanthanum sulfate, lanthanum chloride, lanthanum nitrate, lanthanum acetate, and lanthanum carbonate. The lanthanum compound to be used can deposit a hydroxide or hydrated oxide of lanthanum by reacting with alkali such as an alkali metal hydroxide. It is preferred to use a lanthanum nitrate as a water-soluble lanthanum compound and use a sodium hydroxide solution as alkali which is to react with it. The amount of the lanthanum compound to be used may be in a common range of about 0.01% by mass to about 1.0% by mass, in terms of the total mass of lanthanum, with respect to the titanium dioxide and/or iron oxide to be contained in the metal oxide layer in the present embodiment. In other words, the amount of the lanthanum compound to be used for forming a hydroxide or a hydrated oxide of lanthanum may be in a common range of about 0.01 parts by mass to about 1.0 part by mass, in terms of the total mass of lanthanum, with respect to 100 parts by mass of the titanium dioxide and/or iron oxide to be contained in the metal oxide layer. More preferably, the lanthanum compound is added to an aqueous slurry in an amount of about 0.02% by mass to about 0.5% by mass with respect to the titanium dioxide and/or iron oxide. In other words, the lanthanum compound is contained in an aqueous slurry to be used for forming a hydroxide or a hydrated oxide of lanthanum in an amount of about 0.02 parts by mass to about 0.5 parts by mass, in terms of the total mass of lanthanum, with respect to 100 parts by mass of the titanium dioxide and/or iron oxide contained in the metal oxide layer. The acid or alkali to be used is added to the slurry in an amount sufficient to react with the lanthanum compound to cause deposition of the hydroxide or hydrated oxide of lanthanum on the particles.

<Hydroxide or Hydrated Oxide of Aluminum>

A hydroxide or hydrated oxide of aluminum can be obtained by reacting an acidic or alkaline aluminum compound with an appropriate acid or alkali, so as to be deposited on the particles (the flaky particles covered with titanium dioxide and/or iron oxide) concurrently with the reaction. Examples of the acidic aluminum compound to be used include mineral acid aluminum salts, aluminum chloride, aluminum sulfate, and aluminum nitrate. Examples of an alkaline aluminum compound include alkali metal aluminates such as sodium aluminate. The amount of the acidic or alkaline aluminum compound may be in a common range of about 2% by mass to about 4% by mass, in terms of the total mass of aluminum, with respect to the titanium dioxide and/or iron oxide to be used for the metal oxide layer in the present embodiment. Preferably, the aluminum compound is added to a slurry in an amount of about 2.5% by mass to about 3.5% by mass with respect to the titanium dioxide and/or iron oxide. In other words, the aluminum compound is contained in an aqueous slurry to be used for forming a hydroxide or hydrated oxide of aluminum in an amount of about 2 parts by mass to about 4 parts by mass, more preferably in an amount of about 2.5 parts by mass to about 3.5 parts by mass, in terms of the total mass of aluminum, with respect to 100 parts by mass of the titanium dioxide and/or iron oxide to be contained in the metal oxide layer. An appropriate alkali or acid is added to the slurry in an amount sufficient for deposition of the hydroxide or hydrated oxide of aluminum on the bases concurrently with or following the addition of the aluminum compound.

<Surface Treatment Layer>

It is preferred that a surface treatment layer be formed as the outermost layer, using an organic compound containing an oxazoline ring and/or silane coupling agent in order to improve the adhesion to a coating film matrix resin described later.

Examples of the organic compound containing an oxazoline ring include a polymer containing an oxazoline ring or a polyvalent oxazoline oligomer.

Examples of the polymer containing an oxazoline ring include water-soluble polymers such as EPOCROS WS-500, WS-700, and emulsion polymers such as EPOCROS K-2010, K-2020, K-2030 (manufactured by Nippon Shokubai Co., Ltd.). The water-soluble polymers are particularly preferred because of their high reactivity with a coating film matrix resin containing a carboxyl group.

Specific examples of the polyvalent oxazoline oligomer as a dioxazoline compound include: 1,6-bis(1,3-oxazoline-2-yl)hexane, 1,8-bis(1,3-oxazoline-2-yl) octane, 1,10-bis(1,3-oxazoline-2-yl)decane, 1,3-bis(1,3-oxazoline-2-yl)cyclohexane, 1,4-bis(1,3-oxazoline-2-yl)cyclohexane, 2,2'-(1,3-phenylene)-bis(2-oxazoline), 2,2'-(1,4-phenylene)-bis(2-oxazoline), 2,2'-(1,2-phenylene)-bis(2-oxazoline), 2,2'-(1,3-phenylene)-bis(4-methyl-2-oxazoline), 2,2'-(1,4-phenylene)-bis(4-methyl-2-oxazoline), 2,2'-(1,2-phenylene)-bis(5-methyl-2-oxazoline), 2,2'-(1,3-phenylene)-bis(5-methyl-2-oxazoline), 2,2'-(1,4-phenylene)-bis(5-methyl-2-oxazoline), 2,2'-(1,3-phenylene)-bis(4-methylphenyl-2-oxazoline), 2,2'-(1,4-phenylene)-bis(4-methylphenyl-2-oxazoline), 2,2'-(1,3-phenylene)-bis(4-chlorophenyl-2-oxazoline), and 2,2'-(1,4-phenylene)-bis(4-chlorophenyl-2-oxazoline). One of those dioxazoline compounds may be used, or two or more of them may be used in combination.

Further, examples of the other polyvalent oxazoline oligomers include trioxazoline compounds having three oxazoline groups in one molecule, such as 2,2'-(1,2,4-phenylene)-tris-(2-oxazoline). Two or more of those trioxazoline compounds may be used in combination.

The mass percentage of the organic compound containing an oxazoline ring with respect to the total mass (mass of the whole bright pigment) is preferably 0.01 to 5.0% by mass. If this percentage is less than 0.01% by mass, the compound cannot cover the bright pigment sufficiently, and thus may fail to have the adhesion to the coating film matrix resin. On the other hand, if this percentage is more than 5.0% by mass, the bright pigment may agglomerate, resulting in lack of proper glittering appearance.

The silane coupling agent may be at least one selected from a vinyl group-containing silane, epoxy group-containing silane, methacryloxy group-containing silane, amino group-containing silane, isocyanate group-containing silane, mercapto group-containing silane, and alkoxysilane.

Examples of the vinyl group-containing silane include vinyltrichlorosilane, vinyltrimethoxysilane, and vinyltriethoxysilane.

Examples of the epoxy group-containing silane include 2-(3,4-epoxycyclohexyl)ethyltrimethoxysilane, 3-glycidoxy propyltrimethoxysilane, 3-glycidoxy propylmethyldiethoxysilane, and 3-glycidoxy propyltriethoxysilane.

Examples of the methacryloxy group-containing silane include 3-methacryloxy propylmethyldimethoxysilane, 3-methacryloxy propyltrimethoxysilane, 3-methacryloxy propylmethyldiethoxysilane, and 3-methacryloxy propyltriethoxysilane.

Examples of the amino group-containing silane include N-2(aminoethyl)3-aminopropylmethyldimethoxysilane, N-2(aminoethyl)3-aminopropyltrimethoxysilane, 3-aminopropyltrimethoxysilane, 3-aminopropyltriethoxysilane, 3-triethoxysilyl-N-(1,3-dimethyl-butylidene) propylamine, and N-phenyl-3-aminopropyltrimethoxysilane.

Examples of the isocyanate group-containing silane include 2-isocyanate ethyltrimethoxysilane, 2-isocyanate ethyltriethoxysilane, 3-isocyanate propyltrimethoxysilane, and 3-isocyanate propyltriethoxysilane.

Examples of the mercapto group-containing silane include 3-mercapto propyltrimethoxysilane.

Examples of the alkoxysilane include trimethylmethoxysilane, trimethylethoxysilane, dimethyldimethoxysilane, dimethyldiethoxysilane, methyltrimethoxysilane, methyltriethoxysilane, methyldimethoxysilane, methyldiethoxysilane, dimethylethoxysilane, dimethylvinylmethoxysilane, dimethylvinylethoxysilane, methylvinyldimethoxysilane, methylvinyldiethoxysilane, diphenyldimethoxysilane, diphenyldiethoxysilane, phenyltrimethoxysilane, phenyltriethoxysilane, tetramethoxysilane, and tetraethoxysilane.

The mass percentage of the silane coupling agent with respect to the total mass (mass of the whole bright pigment) is preferably 0.01 to 5.0% by mass. If this percentage is less than 0.01% by mass, a sufficient affinity between a resin and a bright pigment in a bright paint composition may not be achieved. On the other hand, if this percentage is more than 5.0% by mass, a reaction may take place between coupling agents, thus decreasing the affinity between the bright pigment and the resin or the like. In addition, the cost for providing the bright pigments increases.

Subsequently, an example of the bright paint composition of the present invention is described. The bright paint composition of the present embodiment can be produced by mixing the above-described bright pigment of the present embodiment with a vehicle.

(Vehicle)

Examples of the main component of the vehicle to be contained in the bright paint composition of the present invention include a resin and a solvent.

It is preferred to use a resin containing a carboxyl group (hereinafter, also referred to as "carboxyl group-containing resin") as the resin. If the vehicle of the bright paint composition of the present invention contains a carboxyl group-containing resin, a metallic layer can be formed, having not only high hardness and excellent abrasion resistance and chemical resistance, but also good adhesion to an adherend. The concentration of the resin in the vehicle is not specifically limited, but is, for example, preferably 10 to 70% by mass, more preferably 25 to 50% by mass, with respect to the total amount of the bright paint composition.

Examples of the carboxyl group-containing resin include carboxyl group-containing acrylic acid polymers such as acrylic acid resins (homopolymers), (meth)acrylic acid copolymers, ethylene-(meth)acrylic acid copolymers, vinyl acetate-(meth)acrylic acid copolymers, (meth)acrylate ester-(meth)acrylic acid copolymers, and styrene-(meth)acrylic acid copolymers. Other examples thereof include styrene-butadiene copolymers (styrene-butadiene latex with a carboxyl group introduced thereto, for example), styrene-maleic anhydride copolymers, carboxyl group-containing urethane resins, carboxyl group-containing polyester resins, carboxyl group-containing alkyd resins, and carboxyl group-containing polyvinyl alcohol resins. Still other examples thereof include natural resins such as carboxymethyl cellulose. Further, two-component resins, such as acrylic-modified polyesters, acrylic-modified polyurethanes, and acrylic-modified epoxy resins, also can be used. Hereinafter, carboxyl group-containing acrylic acid polymers and acrylic-modified epoxy resins are described in detail.

<Carboxyl Group-Containing Acrylic Acid Polymer>

Carboxyl group-containing acrylic acid polymers can be obtained by copolymerization of, for example, acrylic acid esters with aromatic vinyls or vinyl esters. The content of structural units derived from monomers (monomers containing a carboxyl group, wherein the monomers may be salts) in the carboxyl group-containing acrylic acid polymer is, for example, preferably 0.2 to 30% by mass, more preferably 1 to 20% by mass. The acid value of the carboxyl group-containing acrylic acid polymer is preferably 2 to 200 mg KOH/g, more preferably 10 to 100 mg KOH/g.

The weight average molecular weight of the carboxyl group-containing acrylic acid polymer is, for example, preferably 1000 to 1000000, more preferably 3000 to 500000, still more preferably 5000 to 100000. The glass transition temperature of the carboxyl group-containing acrylic acid polymer varies depending on the application of the resin composition, but the temperature of −60° C. to 50° C. generally is preferred.

The bright paint composition preferably contains a carboxyl group-containing acrylic acid polymer having a glass transition temperature of −10° C. to 50° C.

<Acrylic-Modified Epoxy Resin>

In an acrylic-modified epoxy resin, an acrylic vinyl copolymer is introduced to an epoxy resin as a main chain, and the carboxyl groups are bonded with the vinyl copolymer.

An acrylic-modified epoxy resin containing a carboxyl group can be obtained by esterification reaction between a vinyl copolymer and an epoxy resin in a hydrophilic organic solvent in the presence of a basic compound. There is no particular limit to ethylenically unsaturated carboxylic acid monomers that are the source materials of the vinyl copolymer. Examples thereof include acrylic acid, methacrylic acid, maleic acid, fumaric acid, and itaconic acid. Two or more of those may be used. There is no particular limit to the method for polymerizing those monomer components. For example, they may be polymerized using a commonly-used radical polymerization initiator such as azobisisobutyronitrile, and benzoyl peroxide.

The epoxy resin is preferably at least one selected from the group consisting of a bisphenol F type epoxy resin, a bisphenol A type epoxy resin, and a hydrogenated bisphenol A type epoxy resin. In addition, the epoxy resin preferably has an average of 1.1 to 2.0 epoxy groups in one molecule, as well as a number average molecular weight of 900 or more.

The weight average molecular weight of the acrylic-modified epoxy resin is, for example, preferably 2000 to 100000. The acrylic-modified epoxy resin having a weight average molecular weight of 2000 to 100000 has excellent emulsification dispersion performance, and thus gelation thereof hardly occurs during the reaction between the acrylic vinyl copolymer and the epoxy resin.

<Solvent>

In the case where the solvent contained in the vehicle is an organic solvent, examples of the organic solvent include: alcohols (such as methanol, ethanol, propanol, isopropanol, and n-butanol); aliphatic hydrocarbons (such as hexane, heptane, octane); alicyclic hydrocarbons (such as cyclohexane); aromatic hydrocarbons (such as benzene, toluene, xylene); esters (such as ethyl acetate, n-butyl acetate, isobutyl acetate, and n-butyl acetate); ketones (such as acetone, methyl ethyl ketone, and methyl isobutyl ketone); ethers (such as diethyl ether, dioxane, and tetrahydrofuran); cellosolves (such as methyl cellosolve (ethylene glycol monomethyl ether), ethyl cellosolve, propyl cellosolve, butyl cellosolve, phenyl cellosolve, and benzyl cellosolve); and carbitols (such as diethylene glycol monomethyl ether, carbitol (diethylene glycol monoethyl ether), and diethylene glycol monopropyl ether). A mixed solvent thereof also can be used.

In the case where the solvent contained in the vehicle is water, if the vehicle further contains alkali, the resin can be dissolved in water. Examples of the alkali include: organic bases such as aliphatic amines (e.g., trimethylamine, triethylamine, ethylenediamine); alkanolamines such as ethanolamine, diethanolamine, dimethylethanolamine, triethanolamine; heterocyclic amines such as morpholine; ammonia; and inorganic bases such as alkali metal compounds (e.g., sodium hydroxide, and potassium hydroxide). Among those, ammonia, diethanolamine, dimethylethanolamine, and triethanolamine are preferred.

In the case where the solvent contained in the vehicle is water, it is desired that the acidic group (e.g., a carboxyl group) contained in the resin (e.g., carboxyl group-containing acrylic acid polymer) be neutralized by a base to the extent that the resin can be water-dispersed. The percentage of the acidic groups to be neutralized is desirably about 50% of all the acidic groups. For example, supposing that the total number of moles of the acidic groups contained in the resin is 1, amine with 0.4 to 2.0 times the number of moles, preferably amine with 0.6 to 1.4 times the number of moles, may be used for the neutralization of the acidic groups.

The aqueous emulsion can be prepared by a commonly-used method. One example is a method in which a part of the carboxyl groups in the carboxyl group-containing acrylic acid polymer is neutralized by a base for dispersion of the carboxyl group-containing acrylic acid polymer in water. The aqueous emulsion may be prepared by an emulsion polymerization method. For the emulsion polymerization, commonly-used emulsifying agents (for example, anionic surfactants, nonionic surfactants, and protective colloids such as polyvinyl alcohols and water-soluble polymers) may be used. The pH of the aqueous emulsion may be adjusted using a pH adjuster.

<<Cross-Linking Curing Agent>>

The vehicle constituting the bright paint composition of the present invention further may contain a cross-linking curing agent. As a cross-linking curing agent, an amino resin and/or a polyisocyanate compound can be used. When the resin constituting the vehicle has a hydroxyl group, this hydroxyl group reacts with a cross-linking agent such as an amino resin and a polyisocyanate compound, thereby allowing the resin to be cured. The amino resin and/or the polyisocyanate compound undergoes a cross-linking reaction also with a carboxyl group, an amino group, and the like having active hydrogen besides the hydroxyl group.

Examples of the amino resin that is an example of the cross-linking curing agent include melamine resins such as an alkyletherified melamine resin, benzoguanamine resins such as an alkyletherified benzoguanamine resin, and urea resins such as an alkyletherified urea resin. Among those, melamine resins are preferred. Specific examples of the melamine resins include dimethylol melamine, trimethylol melamine, tetramethylol melamine, pentamethylol melamine, and hexamethylol melamine. Furthermore, the amino resins may be alkyl-etherified (e.g., methyl ether, ethyl ether, propyl ether, isopropyl ether, butyl ether, isobutyl ether, etc.) products of those melamine resins, urea-formamide condensation products, or urea-melamine condensation products. Two or more of those amino resins may be used in combination.

It is preferred that the content of the amino resin be set, for example, so that the mass ratio between the resin (solid content) that constitutes the vehicle and the amino resin (solid content) is 95/5 to 60/40. It is more preferable that the content thereof be set so that the mass ratio is 85/15 to 65/35. This allows the coating film formed by applying the paint to have high strength as well as high corrosion resistance.

As a polyisocyanate compound that is an example of the cross-linking curing agent, for example, a blocked polyisocyanate compound in which the isocyanate groups are masked with a blocking agent is suitable. Examples of the polyisocyanate compound include HDIs (such as hexamethylene diisocyanate), TDIs (such as tolylene diisocyanate), XDIs (such as xylylene diisocyanate), and MDIs (such as diphenylmethane diisocyanate). Examples of the blocking agent include oxime and lactam.

When the above-mentioned polyisocyanate compound is a blocked polyisocyanate compound, it is preferred that the content thereof be set so that the molar ratio between the hydroxyl groups contained in the resin constituting the vehicle and the deblocked and regenerated isocyanate groups in the polyisocyanate compound (the number of moles of hydroxyl groups/the number of moles of regenerated isocyanate groups) is 100/20 to 100/150.

Other thermoplastic resins (such as an acrylic resin and a polyester resin containing no carboxyl group), thermosetting resins (such as an urethane resin), and additives such as antioxidants, ultraviolet absorbers, stabilizers such as heat stabilizers, plasticizers, antistatic agents, dispersants, anti-skinning agents, viscosity modifiers such as thickeners, planarizers, antidripping agents, fungicides, preservatives, fillers, dyes and pigments (such as phthalocyanine pigment, perylene pigment, quinacridone pigment, indigo pigment, isoindolinone pigment, colcothar, yellow iron oxide, and carbon black) may be added to the vehicle of the bright paint composition of the present invention depending on the application.

Next, embodiments of the automobile outer panel coating material of the present invention are described below. The automobile outer panel coating material of the present embodiment includes a metallic base layer containing 0.1 to 30% by mass of the above-described bright pigment of the present embodiment. The automobile outer panel coating material of the present embodiment may include other layers (for example, a clear layer that can be produced by applying a clear paint) than the metallic base layer.

In applying the paint to automobile outer panels, there are methods to be employed such as a so-called "two-coat one-bake method" as a general method for forming a laminated coating film, and a so-called "three-coat two-bake method" or a so-called "three-coat one-bake method" as a method for forming a laminated coating film with improved glittering appearance of a bright pigment.

According to the "two-coat one-bake method", first, a metallic base paint called an overcoat (which is equivalent to the bright pigment composition of the present invention) containing a metallic pigment (which is equivalent to the bright pigment of the present invention) is applied onto a coated plate that has been subjected to undercoating and intermediate coating. Next, a clear paint is applied thereto in layers by wet-on-wet coating without curing of the metallic base paint. Finally, the clear coating film and the metallic base coating film are cured simultaneously to form a metallic base layer and a top clear layer.

It is preferred that the bright pigment of the present invention be used for a color base layer having L* of 40 or more in the three-coat method, because the effects of an excellent single color development property and glittering appearance which are not achieved in the conventional bright pigments can be expected.

In the "three-coat two-bake method", a color base paint called an overcoat is applied onto a coated plate that has been subjected to undercoating and intermediate coating, followed by baking and curing, to form a color base layer having L* of 40 or more. Subsequently, a metallic base paint containing a metallic pigment is applied thereto, and a clear paint is applied in layers by wet-on-wet coating without curing of the metallic base paint. Finally, the clear coating film and the metallic base coating film are cured simultaneously to form a metallic base layer and a top clear layer.

In the "three-coat one-bake method", a color base paint called an overcoat is applied (L* of 40 or more) onto a coated plate that has been subjected to undercoating and intermediate coating, and a metallic base paint containing a metallic pigment is applied thereto without baking or curing of the color base paint. Subsequently, a clear paint is applied in layers by wet-on-wet coating without curing of the metallic base paint as well. Finally, the clear coating film, the metallic base coating film, and the color base coating film are cured simultaneously to form a color base layer, a metallic base layer, and a top clear layer.

Figure 3:
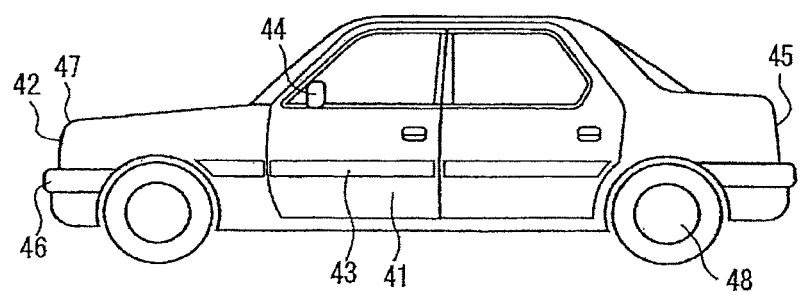
FIG. 3 is a side view of an example of an automobile having an example of an automobile outer panel coating material of the present invention.

Examples of the automobile outer panel coating material of the present invention include, as shown in FIG. 3, an outer panel 41 that is the exterior of an automobile, a radiator grille 42, side moldings 43, door mirrors 44, a back panel 45, a bumper 46, an emblem 47, wheel covers 48, and the like. Hereinafter, an example of the automobile outer panel coating material of the present invention is described by way of the example of the outer panel 41.

Figure 4:
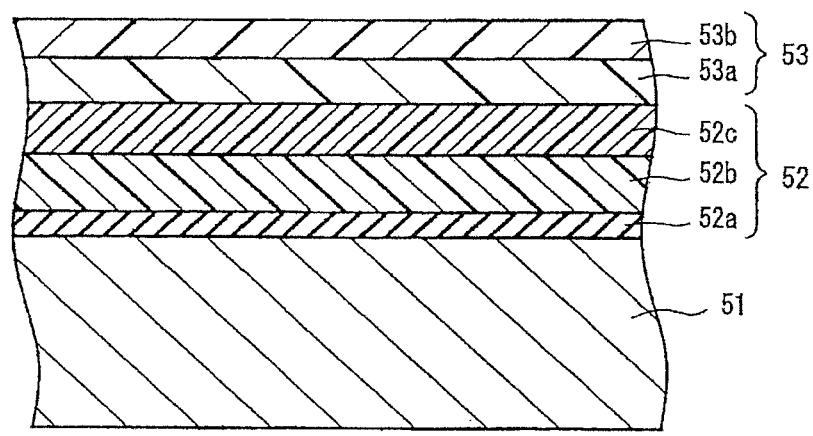
FIG. 4 is a schematic sectional view of an example of the automobile outer panel coating material of the present invention.

In the outer panel, as shown in FIG. 4, an undercoat portion 52 and an overcoat portion 53 are formed in this order on one main surface of a steel plate 51 (base material to be coated for an automobile outer panel). The undercoat portion 52 includes a chemical conversion layer 52a, a cationic electrodeposition layer 52b, and an intermediate coat layer 52 c in this order from the side of the steel plate 51. In the case of employing the two-coat one-bake method, the overcoat portion 53 includes a metallic base layer 53a containing the bright pigment of the present invention and a clear layer 53b in this order from the side of the steel plate 51. An example of the automobile outer panel coating material of the present invention includes the metallic base layer 53a that is formed through use of a composition containing the bright pigment of the present invention (bright paint composition of the present invention). Therefore, the automobile outer panel coating material is excellent in a single color development property of flaky particles and has an outer appearance with a satisfactory coating film finishing property.

In the present invention, the material and formation method for the chemical conversion layer 52a, the cationic electrodeposition layer 52b, the intermediate layer 52c, and the top clear layer 53b are not specifically limited and may be the same as the conventionally known ones. The following is an example for each layer.

The chemical conversion layer 52a is provided so as to prevent the corrosion of the steel plate 51. The chemical conversion layer 52a is composed of, for example, a zinc phosphate covering film.

The cationic electrodeposition layer 52b is provided so as to improve the corrosion resistance of the steel plate 51 as well as the stability of layers to be formed above the cationic electrodeposition layer 52b, and to facilitate the formation of the layers to be formed above the cationic electrodeposition layer 52b. The cationic electrodeposition layer 52b is composed of, for example, a cured coating film containing an acrylic/urethane resin.

The intermediate coat layer 52c is provided so as to enhance the adhesion between the layer below the intermediate coat layer 52c and the layer above it, and to improve the chipping resistance of the layer above the intermediate coat layer 52c. The intermediate coat layer 52c is composed of, for example, a cured coating film containing an acrylic/melamine resin.

The top clear layer 53b is provided so as to impart a lustrous outer appearance, and to improve the fouling resistance. The clear layer 53b is composed of, for example, a cured coating film containing an acrylic/melamine resin.

EXAMPLES

Hereinafter, the present invention is described in further detail by way of examples and comparative examples; however, the present invention is not limited to the following description.

Tables 4 to 6 show compositions of flaky glass particles, flaky alumina particles, and synthetic mica particles used in examples and comparative examples.

TABLE 4

| Composition of flaky glass particles | | | | |
|---|---|---|---|---|
| | Example 6 | Examples 1 to 5, 11, 12 Comparative Examples 1, 2 | Example 10 C glass | Example 9 WO2006/68255 |
| $SiO_2$ | 65.4 | 64 | 66.8 | 61.8 |
| $Al_2O_3$ | 11 | 11 | 4.7 | 11.2 |
| CaO | 15 | 10.3 | 6.6 | 21.8 |
| MgO | 2.3 | 2.9 | 2.6 | 3 |
| $B_2O_3$ | 0 | 0 | 4.1 | — |
| $Na_2O$ | 3.8 | 8.9 | 10.3 | 0.4 |
| $K_2O$ | 0.5 | 0.8 | 0.8 | 0.3 |
| $Li_2O$ | 1.9 | 2 | 0.6 | — |
| ZnO | 0.1 | 0.1 | 3.6 | — |
| $TiO_2$ | — | — | — | 1.6 |
| $FeO/Fe_2O_3$ | — | — | 0 | — |

TABLE 4-continued

Composition of flaky glass particles

| | Example 6 | Examples 1 to 5, 11, 12 Comparative Examples 1, 2 | Example 10 C glass | Example 9 WO2006/68255 |
|---|---|---|---|---|

(Unit: % by mass)

TABLE 5

Composition of flaky alumina particles

| | Example 7 | Comparative Example 3 |
|---|---|---|
| $Al_2O_3$ | 92.8 | 78.5 |
| $Na_2O$ | 4.2 | 1.3 |
| $K_2O$ | 2 | 17.4 |
| $TiO_2$ | — | 1 |
| $P_2O_5$ | 1 | 1.8 |

(Unit: % by mass)

TABLE 6

Composition of synthetic mica particles

| | Comparative Example 4 Fluorine gold mica $KMg_3(AlSi_3O_{10})F_2$ | Example 8 Sodium tetrasilicon mica $NaMg_{2.5}(Si_4O_{10})F_2$ |
|---|---|---|
| $SiO_2$ | 43 | 60.8 |
| $Al_2O_3$ | 10.5 | — |
| MgO | 29.1 | 24.6 |
| $Na_2O$ | 0.9 | 4.1 |
| $K_2O$ | 7.5 | — |
| F | 9 | 10.5 |

(Unit: % by mass)

Example 1

A bright pigment of Example 1 is flaky glass particles (refractive index: 1.53, average thickness: 0.45 μm, and minimum thickness: 0.26 μm) each covered with rutile titanium dioxide.

First, a tapered cup 22 attached to a variable-speed electric motor was rotated at predetermined speed by an apparatus shown in FIG. 2 for producing flaky glass through use of a flow of molten glass, and molten glass was poured into the cup 22 from above. The molten glass in the cup 22 was sent outside beyond a rim 23 due to centrifugal force and crushed into small flaky glass while being kept in a plate shape by an airflow. The flaky glass thus obtained was collected in a chamber 26. Then, the flaky glass was sent to a cyclone collection/filtration section and cooled to be solidified. The flaky glass thus obtained was pulverized through use of a jet mill type pulverizer with the intention that the flaky glass had an average particle diameter of 40 μm. Thus, flaky glass particles having an average particle diameter D50 of 40.1 μm were produced. Factors for determining a thickness distribution are the stability of a flow rate of molten glass, the distance between plates 24, 25, the speed of an airflow between the plates 24, 25, and the like.

The flaky glass particles were classified. Using a sieve with a mesh opening of 45 μm, and arranging a receiving tray below the sieve, the flaky glass particles were sieved for a predetermined period of time so that coarse particles were removed. The flaky glass particles collected by the receiving tray each were obtained as a base material (a flaky particle) of the bright pigment of the present example. The particle size distribution, refractive index, and thickness of the flaky glass particles thus obtained were measured. The average particle diameter (D50) was 24.1 μm; D90 was 44.0 μm; the refractive index was 1.53; the average thickness was 0.45 μm; and the minimum thickness was 0.26 μm. The zeta potential of the flaky glass in a hydrochloric acid aqueous solution (pH=2.0) was −19 mV.

Next, the classified flaky glass was coated with tin oxide (catalytic nucleus), and thereafter was covered with titanium dioxide. The catalytic nucleus refers to a substance to be a catalyst for deposition of a covering film. Specifically, the following was performed.

First, 3 L of ion-exchanged water at room temperature was adjusted to pH 1.6 with hydrochloric acid while stirring, and 300 g of flaky glass particles were added to the resultant to obtain a slurry. To this slurry, a tin solution, in which 2 g of stannic chloride has been dissolved in 30 mL of a hydrochloric acid aqueous solution of pH 2 in advance, were added quantitatively at a rate of 1.5 ml per minute. Then, while this state was kept for 20 minutes, the flaky glass particles were subjected to a surface treatment with tin oxide.

Then, the resultant slurry was heated to 75° C. while adjusting the pH to 1.0 with 35% by mass of a hydrochloric acid aqueous solution. While stirring, an aqueous titanium tetrachloride solution (containing 16.5% by mass of titanium) was added quantitatively at a rate of 2.0 mL/minute to the obtained slurry for forming a metal oxide layer, and caustic soda obtained by dissolving sodium hydroxide in an amount of 10% by mass was added so as to keep the pH of the slurry for forming a metal oxide layer to be 1.0. Caustic soda continued to be added until a product having glittering appearance and a silver pearl tone was obtained.

After a product with the target color tone was obtained, the product was collected by filtration under reduced pressure, washed with pure water, dried at 150° C., and baked at 600° C.

Thus, the bright pigment of Example 1, in which flaky glass was covered with a layer (metal oxide layer) substantially made of titanium dioxide, was obtained through the above-mentioned method.

The obtained bright pigment of Example 1 had an average particle diameter (D50) of 24.5 μm, D90 of 44.1 μm, a specific surface area of 1.7 m²/g, a thickness variation coefficient of a titanium dioxide layer of 7.4%, and a residue on sieve of 0.02% by mass. The obtained bright pigment was dissolved in hydrofluoric acid and subjected to ICP analysis. As a result, the content of $Na_2O$ contained in flaky particles obtained by removing the metal oxide layer from the bright pigment was 8.7% by mass. The sieve residual is obtained by a residue-on-sieve method (in accordance with JIS-K-5101) (see <Evaluation of filtration property> described later).

Example 2

A bright pigment of Example 2 is flaky glass particles (refractive index: 1.53, average thickness: 0.35 μm, and minimum thickness: 0.16 μm) each covered with rutile titanium dioxide.

First, flaky glass was obtained by the same method as that of Example 1 except that the flaky glass was produced so as to have an average thickness of 0.35 μm through use of the apparatus of FIG. 2. The flaky glass thus obtained was pulverized through use of a jet mill type pulverizer with the intention that the flaky glass had an average particle diameter of 40 μm. Thus, flaky glass particles having an average particle diameter D50 of 40.9 μm were produced.

The flaky glass particles were classified in the same way as in Example 1, and the flaky glass particles collected by the receiving tray each were obtained as a base material (a flaky particle) of the bright pigment of the present example. The flaky glass particles thus obtained had an average particle diameter (D50) of 24.3 μm, D90 of 44.1 μm, a refractive index of 1.53, an average thickness of 0.35 μm, and a minimum thickness of 0.16 μm. The zeta potential of the flaky glass in a hydrochloric acid aqueous solution (pH=2.0) was −19 mV.

Then, flaky glass particles covered with a titanium dioxide layer (metal oxide layer) having glittering appearance and a silver pearl tone were obtained as the bright pigment of Example 2 in the same way as in Example 1. The obtained bright pigment of Example 2 had an average particle diameter (D50) of 24.6 μm, D90 of 44.3 μm, a specific surface area of 1.7 $m^2/g$, a thickness variation coefficient of a titanium dioxide layer of 7.4%, and a residue on sieve of 0.03% by mass. The obtained bright pigment was dissolved in hydrofluoric acid and subjected to ICP analysis. As a result, the content of $Na_2O$ contained in flaky particles obtained by removing the metal oxide layer from the bright pigment was 8.7% by mass.

Example 3

A bright pigment of Example 3 is flaky glass particles (refractive index: 1.53, average thickness: 0.55 μm, and minimum thickness: 0.35 μm) each covered with rutile titanium dioxide.

First, flaky glass was obtained by the same method as that of Example 1 except that the flaky glass was produced so as to have an average thickness of 0.55 μm through use of the apparatus of FIG. 2. The flaky glass thus obtained was pulverized through use of a jet mill type pulverizer with the intention that the flaky glass had an average particle diameter of 40 μm. Thus, flaky glass particles having an average particle diameter D50 of 40.5 μm were produced.

The flaky glass particles were classified in the same way as in Example 1, and the flaky glass particles collected by the receiving tray each were obtained as a base material (a flaky particle) of the bright pigment of the present example. The flaky glass particles thus obtained had an average particle diameter (D50) of 24.4 μm, D90 of 44.2 μm, a refractive index of 1.53, an average thickness of 0.55 μm, and a minimum thickness of 0.35 μm. The zeta potential of the flaky glass particles in a hydrochloric acid aqueous solution (pH=2.0) was −19 mV.

Then, flaky glass particles covered with a titanium dioxide layer (metal oxide layer) having glittering appearance and a silver pearl tone were obtained as the bright pigment of Example 3 in the same way as in Example 1.

The obtained bright pigment of Example 3 had an average particle diameter (D50) of 24.6 μm, D90 of 44.3 μm, a specific surface area of 1.7 $m^2/g$, a thickness variation coefficient of a titanium dioxide layer of 7.4%, and a residue on sieve of 0.03% by mass. The obtained bright pigment was dissolved in hydrofluoric acid and subjected to ICP analysis. As a result, the content of $Na_2O$ contained in flaky particles obtained by removing the metal oxide layer from the bright pigment was 8.7% by mass.

Example 4

A bright pigment of Example 4 is flaky glass particles (refractive index: 1.53, average thickness: 0.45 μm, and minimum thickness: 0.25 μm) each covered with rutile titanium dioxide.

First, flaky glass was obtained by the same method as that of Example 1 except that the flaky glass was produced so as to have an average thickness of 0.45 μm through use of the apparatus of FIG. 2. The flaky glass thus obtained was pulverized through use of a jet mill type pulverizer with the intention that the flaky glass had an average particle diameter of 35 μm. Thus, flaky glass particles having an average particle diameter D50 of 35.8 μm were produced.

The flaky glass particles were classified in the same way as in Example 1, and the flaky glass particles collected by the receiving tray each were obtained as a base material (a flaky particle) of the bright pigment of the present example. It should be noted that a mesh size of a sieve was set to 38 μm. The flaky glass particles thus obtained had an average particle diameter (D50) of 21.4 μm, D90 of 35.4 μm, a refractive index of 1.53, an average thickness of 0.45 μm, and a minimum thickness of 0.25 μm. The zeta potential of the flaky glass in a hydrochloric acid aqueous solution (pH=2.0) was −19 mV.

Then, flaky glass particles covered with a titanium dioxide covering film (metal oxide layer) having glittering appearance and a silver pearl tone were obtained as the bright pigment of Example 4 in the same way as in Example 1.

The obtained bright pigment of Example 4 had an average particle diameter (D50) of 21.8 μm, D90 of 35.8 μm, a specific surface area of 1.7 $m^2/g$, a thickness variation coefficient of a titanium dioxide layer of 7.4%, and a residue on sieve of 0.01% by mass. The obtained bright pigment was dissolved in hydrofluoric acid and subjected to ICP analysis. As a result, the content of $Na_2O$ contained in flaky particles obtained by removing the metal oxide layer from the bright pigment was 8.7% by mass.

Example 5

A bright pigment of Example 5 is flaky glass particles (refractive index: 1.53, average thickness: 0.45 μm, and minimum thickness: 0.25 μm) each covered with rutile titanium dioxide.

First, flaky glass was obtained by the same method as that of Example 1 except that the flaky glass was produced so as to have an average thickness of 0.45 μm through use of the apparatus of FIG. 2. The flaky glass thus obtained was pulverized through use of a jet mill type pulverizer with the intention that the flaky glass had an average particle diameter of 45 μm. Thus, flaky glass particles having an average particle diameter D50 of 46.8 μm were produced.

The flaky glass particles were classified in the same way as in Example 1, and the flaky glass particles collected by the receiving tray each were obtained as a base material (a flaky particle) of the bright pigment of the present example. The particle size distribution, refractive index, and thickness of the flaky glass particles thus obtained were measured to find that the flaky glass particles had an average particle diameter (D50) of 28.4 μm, D90 of 49.0 μm, a refractive index of 1.53, an average thickness of 0.45 μm, and a minimum thickness of 0.25 μm. The zeta potential of the flaky glass particles in a hydrochloric acid aqueous solution (pH=2.0) was −19 mV.

Then, flaky glass covered with a titanium dioxide covering film (metal oxide layer) having glittering appearance and a silver pearl tone were obtained as the bright pigment of Example 5 in the same way as in Example 1.

The obtained bright pigment of Example 5 had an average particle diameter (D50) of 28.9 μm, D90 of 49.7 μm, a specific surface area of 1.7 $m^2/g$, a thickness variation coefficient of a titanium dioxide layer of 7.4%, and a residue on sieve of 0.06% by mass. The obtained bright pigment was dissolved in hydrofluoric acid and subjected to ICP analysis. As a result, the content of $Na_2O$ contained in flaky particles obtained by removing the metal oxide layer from the bright pigment was 8.7% by mass.

Example 6

A bright pigment of Example 6 is flaky glass particles (refractive index: 1.54, average thickness: 0.45 μm, and minimum thickness: 0.25 μm) each covered with rutile titanium dioxide.

First, flaky glass was obtained by the same method as that of Example 1 except that the flaky glass was produced so as to have an average thickness of 0.45 μm through use of the apparatus of FIG. 2. The flaky glass thus obtained was pulverized through use of a jet mill type pulverizer with the intention that the flaky glass had an average particle diameter of 40 μm. Thus, flaky glass particles having an average particle diameter D50 of 41.8 μm were produced.

The flaky glass particles were classified in the same way as in Example 1, and the flaky glass particles collected by the receiving tray each were obtained as a base material (a flaky particle) of the bright pigment of the present example. The flaky glass particles thus obtained had an average particle diameter (D50) of 25.2 μm, D90 of 44.5 μm, a refractive index of 1.54, an average thickness of 0.45 μm, and a minimum thickness of 0.25 μm. The zeta potential of the flaky glass particles in a hydrochloric acid aqueous solution (pH=2.0) was −11 mV.

Then, flaky glass particles covered with a titanium dioxide covering film (metal oxide layer) having glittering appearance and a silver pearl tone were obtained as the bright pigment of Example 6 in the same way as in Example 1.

The obtained bright pigment of Example 6 had an average particle diameter (D50) of 25.4 μm, D90 of 44.7 μm, a specific surface area of 2.8 $m^2/g$, a thickness variation coefficient of a titanium dioxide covering film of 18.3%, and a residue on sieve of 0.04% by mass. The obtained bright pigment was dissolved in hydrofluoric acid and subjected to ICP analysis. As a result, the content of $Na_2O$ contained in flaky particles obtained by removing the metal oxide layer from the bright pigment was 3.7% by mass.

Example 7

A bright pigment of Example 7 is flaky alumina particles (refractive index: 1.76, average thickness: 0.35 μm, and minimum thickness: 0.16 μm) each covered with rutile titanium dioxide.

223.8 g of aluminium sulfate octadecahydrate, 114.5 g of sodium sulfate (anhydride), and 93.7 g of potassium sulfate were added to 450 ml of desalted water and dissolved therein while being heated to about 75° C. After the completion of dissolution, 2.0 g of a titanyl sulfate solution (concentration: 34.4%) were added to the resultant solution to prepare a mixed aqueous solution (a). Separately, 0.9 g of trisodium phosphate dodecahydrate and 107.9 g of sodium carbonate were dissolved in 250 ml of desalted water to prepare a mixed aqueous solution (b). The mixed aqueous solutions (a) and (b) were added to 200 ml of desalted water while stirring at a predetermined speed over about 15 minutes so that the aqueous solutions (a) and (b) became almost equivalent to each other, and the mixture was further stirred for 15 minutes. The solution thus obtained was dried by evaporation and then subjected to a heat treatment at 1,200° C. for 5 hours. Water was added to the treated material thus obtained so as to dissolve a free sulfate in water. Then, an insoluble solid was separated by filtration, washed with water, and dried to obtain flaky alumina particles.

The flaky alumina particles thus obtained had an average particle diameter (D50) of 19.9 μm, D90 of 36.2 μm, a refractive index of 1.76, an average thickness of 0.35 μm, and a minimum thickness of 0.16 μm. The zeta potential of the flaky alumina particles in a hydrochloric acid aqueous solution (pH=2.0) was −13 mV.

Then, flaky alumina particles covered with a titanium dioxide covering film (metal oxide layer) having glittering appearance and a silver pearl tone were obtained as the bright pigment of Example 7 in the same way as in Example 1.

The obtained bright pigment of Example 7 had an average particle diameter (D50) of 20.5 μm, D90 of 36.5 μm, a specific surface area of 2.3 $m^2/g$, a thickness variation coefficient of a titanium dioxide covering film of 18.2%, and a residue on sieve of 0.01% by mass. The obtained bright pigment was dissolved in hydrofluoric acid and subjected to ICP analysis. As a result, the content of $Na_2O$ contained in flaky particles obtained by removing the metal oxide layer from the bright pigment was 3.9% by mass.

Example 8

A bright pigment of Example 8 is synthetic mica (commercially available sodium tetrasilicon mica $NaMg_{2.5}(Si_4O_{10})F_2$, refractive index: 1.58, average thickness: 0.35 μm, minimum thickness: 0.16 μm) each covered with rutile titanium dioxide.

The synthetic mica was classified in the same way as in Example 1, and the synthetic mica collected by the receiving tray was obtained as a base material (a flaky particle) of the bright pigment of the present example. The synthetic mica thus obtained had an average particle diameter (D50) of 20.2 μm, D90 of 34.6 μm, a refractive index of 1.58, an average thickness of 0.35 μm, and a minimum thickness of 0.16 μm. The zeta potential of the synthetic mica in a hydrochloric acid aqueous solution (pH=2.0) was −13 mV.

Then, synthetic mica covered with a titanium dioxide covering film (metal oxide layer) having glittering appearance and a silver pearl tone was obtained as the bright pigment of Example 8 in the same way as in Example 1.

The obtained bright pigment of Example 8 had an average particle diameter (D50) of 20.4 μm, D90 of 35.1 μm, a specific surface area of 2.5 $m^2/g$, a thickness variation coefficient of a titanium dioxide covering film of 18.3%, and a residue on sieve of 0.01% by mass. The obtained bright pigment was dissolved in hydrofluoric acid and subjected to ICP analysis. As a result, the content of $Na_2O$ contained in flaky particles obtained by removing the metal oxide layer from the bright pigment was 3.9% by mass.

Example 9

A bright pigment of Example 9 is flaky glass particles (refractive index: 1.57, average thickness: 0.45 μm, and minimum thickness: 0.26 μm) each covered with rutile titanium dioxide.

First, flaky glass was obtained by the same method as that of Example 1 except that the flaky glass was produced so as to have an average thickness of 0.45 μm through use of the apparatus of FIG. 2. The flaky glass thus obtained was pulverized through use of a jet mill type pulverizer with the intention that the flaky glass had an average particle diameter of 40 μm. Thus, flaky glass particles having an average particle diameter D50 of 41.3 μm were produced.

The flaky glass particles were classified in the same way as in Example 1, and the flaky glass particles collected by the receiving tray each were obtained as a base material (a flaky particle) of the bright pigment of the present example. The flaky glass particles thus obtained had an average particle diameter (D50) of 24.2 μm, D90 of 43.9 μm, a refractive index of 1.57, an average thickness of 0.45 μm, and a minimum thickness of 0.26 μm. The zeta potential of the flaky glass in a hydrochloric acid aqueous solution (pH=2.0) was −4 mV.

Then, flaky glass particles covered with a titanium dioxide covering film (metal oxide layer) having glittering appearance and a silver pearl tone were obtained as the bright pigment of Example 9 in the same way as in Example 1.

The obtained bright pigment of Example 9 had an average particle diameter (D50) of 24.4 μm, D90 of 44.1 μm, a specific surface area of 8.7 m$^2$/g, a thickness variation coefficient of a titanium dioxide covering film of 24.0%, and a residue on sieve of 0.02% by mass. The obtained bright pigment was dissolved in hydrofluoric acid and subjected to ICP analysis. As a result, the content of Na$_2$O contained in flaky particles obtained by removing the metal oxide layer from the bright pigment was 0.4% by mass.

Example 10

A bright pigment of Example 10 is flaky glass (refractive index: 1.52, average thickness: 0.45 μm, and minimum thickness: 0.26 μm) each covered with rutile titanium dioxide.

First, flaky glass was obtained by the same method as that of Example 1 except that the flaky glass was produced so as to have an average thickness of 0.45 μm through use of the apparatus of FIG. 2. The flaky glass thus obtained was pulverized through use of a jet mill type pulverizer with the intention that the flaky glass had an average particle diameter of 40 μm. Thus, flaky glass particles having an average particle diameter D50 of 41.8 μm were produced.

The flaky glass particles were classified in the same way as in Example 1, and the flaky glass particles collected by the receiving tray each were obtained as a base material (a flaky particle) of the bright pigment of the present example. The flaky glass particles thus obtained had an average particle diameter (D50) of 24.5 μm, D90 of 44.2 μm, a refractive index of 1.52, an average thickness of 0.45 μm, and a minimum thickness of 0.26 μm. The zeta potential of the flaky glass particles in a hydrochloric acid aqueous solution (pH=2.0) was −23 mV.

Then, flaky glass particles covered with a titanium dioxide covering film (metal oxide layer) having glittering appearance and a silver pearl tone were obtained as the bright pigment of Example 10 in the same way as in Example 1.

The obtained bright pigment of Example 10 had an average particle diameter (D50) of 24.7 μm, D90 of 44.3 μm, a specific surface area of 1.7 m$^2$/g, a thickness variation coefficient of a titanium dioxide covering film of 7.4%, and a residue on sieve of 0.03% by mass. The obtained bright pigment was dissolved in hydrofluoric acid and subjected to ICP analysis. As a result, the content of Na$_2$O contained in flaky particles obtained by removing the metal oxide layer from the bright pigment was 10.2% by mass.

Comparative Example 1

A bright pigment of Comparative Example 1 is flaky glass particles (refractive index: 1.53, average thickness: 0.30 μm, and minimum thickness: 0.11 μm) each covered with rutile titanium dioxide.

First, flaky glass was obtained by the same method as that of Example 1 except that the flaky glass was produced so as to have an average thickness of 0.30 μm through use of the apparatus of FIG. 2. The flaky glass thus obtained was pulverized through use of a jet mill type pulverizer with the intention that the flaky glass had an average particle diameter of 40 μm. Thus, flaky glass particles having an average particle diameter D50 of 41.7 μm were produced.

The flaky glass particles were classified in the same way as in Example 1, and the flaky glass particles collected by the receiving tray each were obtained as a base material (a flaky particle) of the bright pigment of the present example. The flaky glass particles thus obtained had an average particle diameter (D50) of 24.3 μm, D90 of 44.0 μm, a refractive index of 1.53, an average thickness of 0.30 μm, and a minimum thickness of 0.11 μm. The zeta potential of the flaky glass in a hydrochloric acid aqueous solution (pH=2.0) was −19 mV.

Then, flaky glass particles covered with a titanium dioxide covering film (metal oxide layer) having glittering appearance and a silver pearl tone were obtained as the bright pigment of Comparative Example 1 in the same way as in Example 1.

The obtained bright pigment of Comparative Example 1 had an average particle diameter (D50) of 24.5 μm, D90 of 44.3 μm, a specific surface area of 1.7 m$^2$/g, a thickness variation coefficient of titanium dioxide of 7.4%, and a residue on sieve of 0.03% by mass. The obtained bright pigment was dissolved in hydrofluoric acid and subjected to ICP analysis. As a result, the content of Na$_2$O contained in flaky particles obtained by removing the metal oxide layer from the bright pigment was 8.7% by mass.

Comparative Example 2

A bright pigment of Comparative Example 2 is flaky glass particles (refractive index: 1.53, average thickness: 0.60 μm, and minimum thickness: 0.39 μm) each covered with rutile titanium dioxide.

First, flaky glass was obtained by the same method as that of Example 1 except that the flaky glass was produced so as to have an average thickness of 0.60 μm through use of the apparatus of FIG. 2. The flaky glass thus obtained was pulverized through use of a jet mill type pulverizer with the intention that the flaky glass had an average particle diameter of 40 μm. Thus, flaky glass particles having an average particle diameter D50 of 41.5 μm were produced.

The flaky glass particles were classified in the same way as in Example 1, and the flaky glass particles collected by the receiving tray each were obtained as a base material (a flaky particle) of the bright pigment of the present example. The flaky glass particles thus obtained had an average particle diameter (D50) of 24.2 μm, D90 of 44.2 μm, a refractive index of 1.53, an average thickness of 0.60 μm, and a minimum thickness of 0.39 μm. The zeta potential of the flaky glass in a hydrochloric acid aqueous solution (pH=2.0) was −19 mV.

Then, flaky glass particles covered with a titanium dioxide covering film (metal oxide layer) having glittering appearance and a silver pearl tone were obtained as the bright pigment of Comparative Example 2 in the same way as in Example 1.

The obtained bright pigment of Comparative Example 2 had an average particle diameter (D50) of 24.3 µm, D90 of 44.3 µm, a specific surface area of 1.7 m²/g, a thickness variation coefficient of a titanium dioxide covering film of 7.4%, and a residue on sieve of 0.03% by mass. The obtained bright pigment was dissolved in hydrofluoric acid and subjected to ICP analysis. As a result, the content of Na₂O contained in flaky particles obtained by removing the metal oxide layer from the bright pigment was 8.7% by mass.

Example 11

A bright pigment of Example 11 is flaky glass particles (refractive index: 1.53, average thickness: 0.45 µm, and minimum thickness: 0.26 µm) each covered with rutile titanium dioxide.

First, flaky glass was obtained by the same method as that of Example 1 except that the flaky glass was produced so as to have an average thickness of 0.45 µm through use of the apparatus of FIG. 2. The flaky glass thus obtained was pulverized through use of a jet mill type pulverizer with the intention that the flaky glass had an average particle diameter of 27 µm. Thus, flaky glass particles having an average particle diameter D50 of 26.2 µm were produced.

The flaky glass particles were classified in the same way as in Example 1, and the flaky glass particles collected by the receiving tray each were obtained as a base material (a flaky particle) of the bright pigment of the present example. It should be noted that a mesh size of a sieve was set to 20 µm. The flaky glass particles thus obtained had an average particle diameter (D50) of 20.6 µm, D90 of 33.2 µm, a refractive index of 1.53, an average thickness of 0.45 µm, and a minimum thickness of 0.26 µm. The zeta potential of the flaky glass in a hydrochloric acid aqueous solution (pH=2.0) was −19 mV.

Then, flaky glass particles covered with a titanium dioxide covering film (metal oxide layer) having glittering appearance and a silver pearl tone were obtained as the bright pigment of Example 11 in the same way as in Example 1.

The obtained bright pigment of Example 11 had an average particle diameter (D50) of 21.3 µm, D90 of 33.7 µm, a specific surface area of 1.7 m²/g, a thickness variation coefficient of a titanium dioxide covering film of 7.4%, and a residue on sieve of 0.01% by mass. The obtained bright pigment was dissolved in hydrofluoric acid and subjected to ICP analysis. As a result, the content of Na₂O contained in flaky particles obtained by removing the metal oxide layer from the bright pigment was 8.7% by mass.

Example 12

A bright pigment of Example 12 is flaky glass particles (refractive index: 1.53, average thickness: 0.45 µm, and minimum thickness: 0.26 µm) each covered with rutile titanium dioxide.

First, flaky glass was obtained by the same method as that of Example 1 except that the flaky glass was produced so as to have an average thickness of 0.45 µm through use of the apparatus of FIG. 2. The flaky glass thus obtained was pulverized through use of a jet mill type pulverizer with the intention that the flaky glass had an average particle diameter of 50 µm. Thus, flaky glass particles having an average particle diameter D50 of 51.2 µm were produced.

The flaky glass particles were classified in the same way as in Example 1, and the flaky glass particles collected by the receiving tray each were obtained as a base material (a flaky particle) of the bright pigment of the present example. It should be noted that a mesh size of a sieve was set to 51 µm. The flaky glass particles thus obtained had an average particle diameter (D50) of 32.6 µm, D90 of 52.0 µm, a refractive index of 1.53, an average thickness of 0.45 µm, and a minimum thickness of 0.26 µm. The zeta potential of the flaky glass in a hydrochloric acid aqueous solution (pH=2.0) was −19 mV.

Then, flaky glass particles covered with a titanium dioxide covering film (metal oxide layer) having glittering appearance and a silver pearl tone were obtained as the bright pigment of Example 12 in the same way as in Example 1.

The obtained bright pigment of Example 12 had an average particle diameter (D50) of 33.3 µm, D90 of 52.5 µm, a specific surface area of 1.7 m²/g, a thickness variation coefficient of a titanium dioxide covering film of 7.4%, and a residue on sieve of 0.20% by mass. The obtained bright pigment was dissolved in hydrofluoric acid and subjected to ICP analysis. As a result, the content of Na₂O contained in flaky particles obtained by removing the metal oxide layer from the bright pigment was 8.7% by mass.

Comparative Example 3

A bright pigment of Comparative Example 3 is flaky alumina particles (refractive index: 1.76, average thickness: 0.30 µm, and minimum thickness: 0.11 µm) each covered with rutile titanium dioxide.

First, aluminum hydroxide serving as a starting material was pulverized through use of a ball mill or the like in advance, and the particle size thereof was adjusted so as to obtain an average particle diameter of 3.0 µm. The particles thus obtained were mixed with water to prepare 50% by weight of a slurry. Then, ammonium phosphate was added to the slurry as phosphate anions in an amount of $5.0 \times 10^{-3}$ mol with respect to aluminum hydroxide and thoroughly dissolved in the slurry by mixing.

A pressure vessel was filled with the resultant material. The material was raised in temperature to 600° C. at a temperature rise speed of 0.3° C./min by an electric furnace and kept at a pressure of 150 atmospheres for 3 hours. The vessel was cooled, and the product thus obtained was washed with pure water. Then the product was subjected to filtration sufficiently and dried in a drier at 100° C. for 12 hours to obtain white particle powder (flaky particles). The flaky alumina particles thus obtained had an average particle diameter (D50) of 19.7 µm, D90 of 34.5 µm, a refractive index of 1.76, an average thickness of 0.30 µm, and a minimum thickness of 0.11 µm. The zeta potential of the flaky alumina particles in a hydrochloric acid aqueous solution (pH=2.0) was −5 mV.

Then, flaky alumina particles covered with a titanium dioxide covering film (metal oxide layer) having glittering appearance and a silver pearl tone were obtained as the bright pigment of Comparative Example 3 in the same way as in Example 1.

The obtained bright pigment of Comparative Example 3 had an average particle diameter (D50) of 20.3 µm, D90 of 35.1 µm, a specific surface area of 9.3 m²/g, a thickness variation coefficient of titanium dioxide of 24.2%, and a residue on sieve of 0.01% by mass. The obtained bright pigment was dissolved in hydrofluoric acid and subjected to ICP analysis. As a result, the content of Na$_2$O contained in flaky particles obtained by removing the metal oxide layer from the bright pigment was 0.9% by mass.

Comparative Example 4

A bright pigment of Comparative Example 4 is synthetic mica (commercially available fluorine gold mica KMg$_3$(AlSi$_3$O$_{10}$)F$_2$, refractive index: 1.58, average thickness: 0.25 µm, and minimum thickness: 0.10 µm) covered with rutile titanium dioxide.

The synthetic mica was classified in the same way as in Example 1, and the synthetic mica particles collected by the receiving tray were obtained as a base material (a flaky particle) of the bright pigment of Comparative Example 4. It should be noted that a mesh size of a sieve was set to 45 µm. The flaky synthetic mica particles thus obtained had an average particle diameter (D50) of 19.2 µm, D90 of 34.7 µm, a refractive index of 1.58, an average thickness of 0.25 µm, and a minimum thickness of 0.10 µm. The zeta potential of the flaky synthetic mica in a hydrochloric acid aqueous solution (pH=2.0) was −7 mV.

Then, flaky synthetic mica particles covered with a titanium dioxide covering film (metal oxide layer) having glittering appearance and a silver pearl tone were obtained as the bright pigment of Comparative Example 4 in the same way as in Example 1.

The obtained bright pigment of Comparative Example 4 had an average particle diameter (D50) of 20.1 µm, D90 of 35.1 µm, a specific surface area of 10.5 m$^2$/g, a thickness variation coefficient of titanium dioxide of 25.3%, and a residue on sieve of 0.01% by mass. The obtained bright pigment was dissolved in hydrofluoric acid and subjected to ICP analysis. As a result, the content of Na$_2$O contained in flaky particles obtained by removing the metal oxide layer from the bright pigment was 0.8% by mass.

Further, the crystal structure of titanium dioxide in each of the metal oxide layers of the bright pigments of Examples 1 to 8 and Comparative Examples 1 to 4 was found to be a rutile type as a result of the analysis by a powder X-ray diffraction method.

The samples of the bright pigments of Examples 1 to 12 and Comparative Examples 1 to 4 produced as described above were evaluated for a brightness (luminosity), a coating film finishing property, and uniformity of interference colors by the following methods. Further, a measurement method of a particle diameter distribution and a method for obtaining a thickness direction of flaky particles and the like are described below. Tables 8 and 9 show evaluation results of Examples 1 to 12 and Comparative Examples 1 to 4.

<Measurement Method of Particle Size Distribution>

A laser diffraction particle size distribution analyzer (product name: "Microtrac HRA" manufactured by Nikkiso Co., Ltd.) was used for measuring a particle size distribution. From the measurement results, an average particle diameter (D50) corresponding to a 50% volume-cumulative particle diameter from a small particle diameter side, and an average particle diameter (D90) corresponding to a 90% volume-cumulative particle diameter from a small particle diameter side were determined.

<Thickness Distribution of Flaky Particles>

In the present examples, the thickness "d" (see FIG. 3) was measured with an electronic microscope for any 100 flaky particles to obtain average thickness and minimum thickness.

<Content of Na$_2$O>

0.1 g of flaky particles obtained by removing a metal oxide layer from a bright pigment were weighed precisely and dissolved in 4 ml of perchloric acid (HClO$_4$) and 7.5 ml of hydrofluoric acid. After that, the resultant was solidified by drying and dissolved in 2 ml of hydrochloric acid (1+1). Then, the absorbancy of sodium at a wavelength of 589 nm was measured with a flame spectrophotometer. The content of Na$_2$O contained in flaky particles before the formation of a metal oxide layer was similarly obtained (see Tables 4 to 6).

The amount a(g) of sodium oxide in the sample was calculated by the following expression.

$$a\,(\text{g}) = \text{measurement value (ppm)} \times 10^{-3} \times (100/1000)$$

$$\text{Na}_2\text{O}\,(\%) = (a/W) \times 100$$

W: Collected amount of bright pigment (g)

<Content of TiO$_2$>

First, 0.2 g of a bright pigment was weighed precisely on a platinum plate. Then, 5 ml of perchloric acid was added to the platinum plate, and 10 ml of hydrofluoric acid were further added thereto. The resultant was thoroughly mixed through use of a platinum wire and dissolved by heating on a hot plate, followed by being solidified by drying. After the resultant was allowed to cool, 5 ml of hydrochloric acid (1+1) were added thereto, and the mixture was dissolved by heating. The mixture was cooled and transferred to a 200 ml measuring flask and set to a constant volume of 200 ml. Then, the following "A" (mass of TiO$_2$) was measured by ICP through use of the solution thus obtained.

[ICP Analysis Condition]
Wavelength: 334,941 nm
Carrier gas: 1.0 L/min
Coolant gas: 11.5 L/min
Output: 1.2 KW
Measurement value: 30000×3
Standard sample concentration table (ppm)
Measurement method: Wavelength sequential
(The result is displayed in a unit of "ppm", and hence an average value of n=2 is defined as a measurement value).

$$\text{TiO}_2(\%) = (A \times 10-3 \times 1.6681/W) \times (200/1000) \times 100$$

A: Measurement value
W: Collected amount of bright pigment (g)

<Specific Surface Area of Bright Pigment>

1 g of a bright pigment was weighed precisely and put in a measurement cell and measured for a specific surface area through use of NOVA1000 manufactured by Yuasa Ionics, Inc.

<Zeta Potential>

A plate sample of the same composition as that of flaky particles and a hydrochloric acid aqueous solution of pH 2.0 were prepared in advance, and the zeta potential was measured through use of ELS-6000 manufactured by Otsuka Electronics Co., Ltd. and a plate sample cell by an electrophoretic light scattering method.

<Evaluation of Filtration Property>

Residue-on-sieve method (in accordance with JIS-K-5101)

First, a JIS-Z-8801 standard sieve of 330 mesh (mesh size: 45 µm) is dried at 110° C. and a mass (J1) thereof is measured. Then, 10 g of a bright pigment (sample) is put in a glass container and 50 ml of pure water are added thereto. The mixture is stirred sufficiently, and thereafter, portions of the bright pigment floating in a liquid are transferred onto the sieve. Again, 50 ml of pure water is poured into the remaining sample, and portions of the bright pigment floating in the liquid are transferred onto the sieve in the same way as the above. This operation is repeated several times, whereby the entire sample is transferred onto the sieve. Then, most of the sample is caused to pass through sieve openings by shaking the sieve while pouring pure water to the sample in small amounts. The sample on the sieve is loosened carefully through use of a glass bar as necessary.

The sieve is put in a receiving tray having a diameter of about 120 mm. Pure water is poured into the receiving tray up to 15 mm above a sieve net, and the upper surface of the net is swept through use of a brush. The sieve is pulled up from the tray every 20 times of sweeping of the upper surface of the net, and pure water is flowed out through the sieve openings. Further, the water on the tray is replaced every 40 times of sweeping. When this operation is repeated and the sample is not recognized any more in the water on the tray, a solid substance adhering to the brush is washed off onto the sieve through use of water, and the sieve is washed well. The sieve is dried and a mass (J2) thereof is measured. A residue on sieve I (%) is calculated by the following expression. The following residual amount is obtained by subtracting the mass (J1) of the sieve from the mass (J2) thereof.

$$I=J/S\times 100$$

I: Residue on sieve (%)
J: Mass of residual amount (g)
S: Mass of sample (g)

The residue on sieve I to be used for evaluating a filtration property is preferably 0.2% or less, more preferably 0.1% or less.

<Thickness of Metal Oxide Layer>

The thickness of a metal oxide layer was measured as follows. A bright pigment embedded in a resin and solidified was ruptured, and a cross-section of the resultant was subjected to a conductive treatment by Pt—Pd coating. The cross-section was observed with an electron microscope, and the thickness of the metal oxide layer was measured. Five particles were observed and each thickness of 10 positions was measured for one particle. A thickness variation coefficient of the metal oxide layer was calculated through use of values of a thickness standard deviation and an average thickness determined from the thickness of the metal oxide layer thus obtained.

<Production of Coating Sample>

78% by mass of an acrylic resin (product name: "Acrydic A-322" manufactured by DIC Corporation), 16% by mass of a butylated melamine resin (product name: "Super Beckamine L-117-60" manufactured by DIC Corporation), and 6% by mass of the bright pigment obtained in each of Examples 1 to 12 and Comparative Examples 1 to 4 were mixed with a stirrer, while the viscosity was adjusted to 13 Pa·s (Ford cup No. 4/20° C. manufactured by Yasuda Seiki Seisakusho, Ltd.) by adding an appropriate amount of thinner thereto. Thus, a metallic base paint (bright pigment composition) was prepared. The metallic base paint was applied onto a coated plate (coating color: Munsell color system N=9.5 (CIE L*a*b* color system L*=95)) through use of a spray gun (W-100 manufactured by Anest Iwata Corporation), so that a metallic base coating film was formed thereon.

Subsequently, 72% by mass of an acrylic resin (product name: "Acrydic A-345" manufactured by DIC Corporation) and 28% by mass of a butylated melamine resin (product name: "Super Beckamine L-117-60" manufactured by DIC Corporation) were mixed with a stirrer, while the viscosity was adjusted to 24 Pa·s (Ford cup No. 4/20° C. manufactured by Yasuda Seiki Seisakusho, Ltd.) by adding thinner thereto. Thus, a clear paint was prepared. The clear paint was applied onto the coated plate having the metallic base coating film formed thereon through use of the spray gun (W-100 manufactured by Anest Iwata Corporation), followed by baking (at 140° C. for 30 minutes), so that a metallic base layer and a top clear layer were formed thereon. The thickness of the coating film after the baking was such that the metallic base layer was 15 μm thick, and the top clear layer was 30 μm thick.

<Luminosity L*(−15°)>

The brightness in highlight areas of a bright pigment in a metallic base layer was evaluated through use of a multi-angle color & effect control measurement unit (product name: "BYK-mac" manufactured by BYK-Gardner). The metallic base layer containing a bright pigment has high brightness, reflecting light sufficiently in highlight areas, whereas the metallic base layer becomes dark in shade areas. Thus, an angle change in luminosity and tint called "Flop" occurs.

Figure 5:
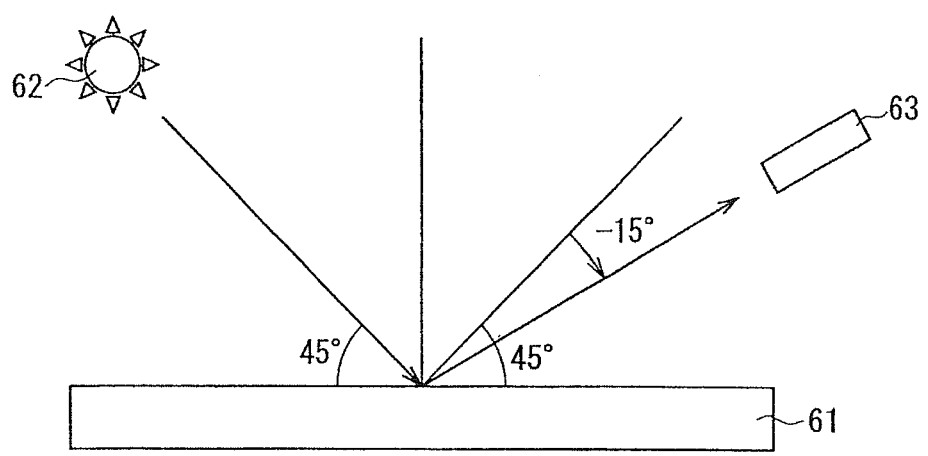
FIG. 5 is a schematic conceptual view illustrating a method for measuring a luminosity $L^*(-15°)$.

As shown in FIG. 5, a light source 62 is provided at a position of 45° from a direction perpendicular to the surface of a coating film 61 (that is, 45° from a film surface), and a coating film surface is irradiated with light from an angle of 45°. At an angle shifted by 15° from a direction of regular reflection of incident light (that is, 45° from the film surface) to an opposite direction of the light source, light reflected from the bright pigment becomes maximum. This position is called "−15°". L*a*b* of reflected light having entered a detector 63 was measured. The luminosity L* is preferably 135 or more, more preferably 140 or more.

<Evaluation of Coating Film Finishing Property>

The coating film finishing property was evaluated through use of a micro-wave-scan (manufactured by BYK-Gardner). The effects on the coating film finishing property caused by the bright pigment were evaluated using a value Wa (0.1 to 0.3 mm). The Wa value is preferably 15 or less, more preferably 10 or less, still more preferably 9.7 or less.

<Evaluation of Single Color Development Property of Coating Film Containing Bright Pigment>

Under a D65 natural light source, the degree of a single color development property was observed by visual inspection. The degree of a single color development property (mixing degree of interference colors) was evaluated as the following three levels. The single color development property is preferably 2 or more, more preferably 3.

3: No interference colors are observed
2: Some interference colors are observed
1: A lot of interference colors are observed

TABLE 7

|  | Example 1 | Example 2 | Example 3 | Example 4 | Example 5 | Example 6 | Example 7 | Example 8 |
|---|---|---|---|---|---|---|---|---|
| Kind of flaky particle | Glass | Glass | Glass | Glass | Glass | Glass | Alumina | Synthetic mica |
| Refractive index of flaky particle | 1.53 | 1.53 | 1.53 | 1.53 | 1.53 | 1.54 | 1.76 | 1.58 |
| Average thickness of flaky particle (μm) | 0.45 | 0.35 | 0.55 | 0.45 | 0.45 | 0.45 | 0.35 | 0.35 |

TABLE 7-continued

|  | Example 1 | Example 2 | Example 3 | Example 4 | Example 5 | Example 6 | Example 7 | Example 8 |
|---|---|---|---|---|---|---|---|---|
| Minimum thickness of flaky particle (μm) | 0.26 | 0.16 | 0.35 | 0.25 | 0.25 | 0.25 | 0.16 | 0.16 |
| Average particle diameter (D50) of flaky particle (μm) | 24.1 | 24.3 | 24.4 | 21.4 | 28.4 | 25.2 | 19.9 | 20.2 |
| Average particle diameter (D90) of flaky particle (μm) | 44.0 | 44.1 | 44.2 | 35.4 | 49.0 | 44.5 | 36.2 | 34.6 |
| Zeta potential of flaky particle (mV) | −19 | −19 | −19 | −19 | −19 | −11 | −13 | −13 |
| Content of $Na_2O$ (% by mass) [Note 1] | 8.7 | 8.7 | 8.7 | 8.7 | 8.7 | 3.7 | 3.9 | 3.9 |
| Kind of metal oxide | Titanium dioxide | Titanium dioxide | Titanium dioxide | Titanium dioxide | Titanium dioxide | Titanium dioxide | Titanium dioxide | Titanium dioxide |
| Average particle diameter (D50) of bright pigment (μm) | 24.5 | 24.6 | 24.6 | 21.8 | 28.9 | 25.4 | 20.5 | 20.4 |
| Average particle diameter (D90) of bright pigment (μm) | 44.1 | 44.3 | 44.3 | 35.8 | 49.7 | 44.7 | 36.5 | 35.1 |
| Specific surface area of bright pigment (m²/g) | 1.7 | 1.7 | 1.7 | 1.7 | 1.7 | 2.8 | 2.3 | 2.5 |
| Thickness variation coefficient of metal oxide layer (%) | 7.4 | 7.4 | 7.4 | 7.4 | 7.4 | 18.3 | 18.2 | 18.3 |
| Filtration property (%) | 0.02 | 0.03 | 0.03 | 0.01 | 0.06 | 0.04 | 0.01 | 0.01 |
| Luminosity L*(−15°) | 143.3 | 143.8 | 141.6 | 142.1 | 143.5 | 143.3 | 140.3 | 140 |
| Coating film finishing property (Wa) | 9.6 | 9.3 | 9.9 | 9.5 | 9.7 | 9.7 | 8.9 | 9.2 |
| Single color development property | 3 | 2 | 3 | 3 | 3 | 3 | 2 | 2 |

[Note 1] Content of $Na_2O$ contained in flaky particles obtained by removing a metal oxide layer from a bright pigment

TABLE 8

|  | Example 9 | Example 10 | Comparative Example 1 | Comparative Example 2 | Example 11 | Example 12 | Comparative Example 3 | Comparative Example 4 |
|---|---|---|---|---|---|---|---|---|
| Kind of flaky particle | Glass | Glass | Glass | Glass | Glass | Glass | Alumina | Synthetic mica |
| Refractive index of flaky particle | 1.57 | 1.52 | 1.53 | 1.53 | 1.53 | 1.53 | 1.76 | 1.58 |
| Average thickness of flaky particle (μm) | 0.45 | 0.45 | 0.30 | 0.60 | 0.45 | 0.45 | 0.30 | 0.25 |
| Minimum thickness of flaky particle (μm) | 0.26 | 0.26 | 0.11 | 0.39 | 0.26 | 0.26 | 0.11 | 0.10 |
| Average particle diameter (D50) of flaky particle (μm) | 24.2 | 24.5 | 24.3 | 24.2 | 20.6 | 32.6 | 19.7 | 19.2 |
| Average particle diameter (D90) of flaky particle (μm) | 43.9 | 44.2 | 44.0 | 44.2 | 33.2 | 52.0 | 34.5 | 34.7 |
| Zeta potential of flaky particle (mV) | −4 | −23 | −19 | −19 | −19 | −19 | −5 | −7 |
| Content of $Na_2O$ (% by mass) [Note 1] | 0.4 | 10.2 | 8.7 | 8.7 | 8.7 | 8.7 | 0.9 | 0.8 |
| Kind of metal oxide | Titanium dioxide | Titanium dioxide | Titanium dioxide | Titanium dioxide | Titanium dioxide | Titanium dioxide | Titanium dioxide | Titanium dioxide |
| Average particle diameter (D50) of bright pigment (μm) | 24.4 | 24.7 | 24.5 | 24.3 | 21.3 | 33.3 | 20.3 | 20.1 |
| Average particle diameter (D90) of bright pigment (μm) | 44.1 | 44.3 | 44.3 | 44.3 | 33.7 | 52.5 | 35.1 | 35.1 |
| Specific surface area of bright pigment (m²/g) | 8.7 | 1.7 | 1.7 | 1.7 | 1.7 | 1.7 | 9.3 | 10.5 |
| Thickness variation coefficient of metal oxide layer (%) | 24.0 | 7.4 | 7.4 | 7.4 | 7.4 | 7.4 | 24.2 | 25.3 |
| Filtration property (%) | 0.02 | 0.03 | 0.03 | 0.03 | 0.01 | 0.20 | 0.01 | 0.01 |
| Luminosity L*(−15°) | 132.5 | 143.0 | 134.7 | 131.8 | 132.3 | 134.2 | 132.6 | 130.7 |
| Coating film finishing property (Wa) | 9.6 | 9.7 | 8.9 | 17.5 | 9.4 | 13.3 | 8.8 | 8.8 |

TABLE 8-continued

|  | Example 9 | Example 10 | Comparative Example 1 | Comparative Example 2 | Example 11 | Example 12 | Comparative Example 3 | Comparative Example 4 |
|---|---|---|---|---|---|---|---|---|
| Single color development property | 2 | 3 | 1 | 3 | 3 | 3 | 1 | 1 |

Note 1)
Content of $Na_2O$ contained in flaky particles obtained by removing a metal oxide layer from a bright pigment From the foregoing results (Tables 7 and 8), it is understood that, when a bright pigment containing flaky particles having an average thickness of 0.35 to 0.55 μm and not substantially containing flaky particles having a minimum thickness of 0.15 μm or less is used as in Examples 1 to 12, a coating product excellent in a single color development property can be provided, which has a satisfactory coating finishing property Wa of 15 or less and in which the occurrence of interference color caused by the thickness of the flaky particles is suppressed.

Further, when the minimum thickness of the flaky particles is 0.2 μm or more, and the content of $Na_2O$ in flaky particles to be used for producing a bright pigment is 3 to 11% by mass as in Examples 1, 3 to 6, and 10 to 12, a coating product further excellent in a single color development property can be provided. Further, when D90 of a bright pigment is 30 to 50 μm as in Examples 1 to 10 and 11, a coating product further excellent in a coating finishing property can be provided. Further, when the minimum thickness of flaky particles is 0.2 μm or more, the content of $Na_2O$ is 3% by mass or more and less than 9% by mass (see Tables 4 to 6), and the thickness variation coefficient of a metal oxide layer is 20% or less as in Examples 1 and 3 to 6, a coating product can be provided, which is further excellent in a single color development property and a coating finishing property, and which has high luminosity.

INDUSTRIAL APPLICABILITY

The bright pigment of the present invention can satisfy both an excellent single color development property and a satisfactory coating film finishing property, and hence can be used for various applications such as coating of an automobile outer panel.

The invention claimed is:

1. A bright pigment comprising a flaky particle and a metal oxide layer covering a surface of the flaky particle,
   wherein the metal oxide layer is a single layer formed of at least one material selected from the group consisting of titanium dioxide, reduced titanium oxide, iron oxide, and reduced iron oxide,
   the bright pigment has a particle diameter corresponding to a 90% volume-cumulative particle diameter from a small particle diameter side, in a particle size distribution, of 55 μm or less,
   the flaky particle is formed of a material having a refractive index of 1.4 to 1.8, and
   the flaky particle has an average thickness of 0.35 μm to 0.55 μm and substantially does not contain a flaky particle having a thickness of 0.15 μm or less.

2. The bright pigment according to claim 1, wherein the metal oxide layer has a thickness variation coefficient (thickness standard deviation of the metal oxide layer/average thickness of the metal oxide layer) of 20% or less.

3. The bright pigment according to claim 1, wherein the bright pigment further contains a sodium component.

4. The bright pigment according to claim 3, wherein the sodium component is $Na_2O$, and the flaky particle contains $Na_2O$ in an amount of 3% by mass or more and less than 9% by mass.

5. The bright pigment according to claim 1, wherein the bright pigment has a specific surface area of 3.0 $m^2/g$ or less.

6. The bright pigment according to claim 1, wherein the bright pigment has a particle diameter corresponding to a 90% volume-cumulative particle diameter from a small particle diameter side, in the particle size distribution, of 35 to 50 μm.

7. The bright pigment according to claim 1, wherein a material for the flaky particle is at least one kind selected from the group consisting of glass, silica, alumina, and mica.

8. A bright paint composition comprising the bright pigment according to claim 1.

9. An automobile outer panel coating material comprising a metallic base layer containing 0.1 to 30% by mass of the bright pigment according to claim 1.

10. The automobile outer panel coating material according to claim 9, comprising:
    a color base layer being disposed on one principal surface side of a base material to be coated for an automobile outer panel and having L* of a CIE L*a*b* color system of 40 or more;
    the metallic base layer disposed on the color base layer; and
    a top clear layer disposed on the metallic base layer.

11. A method for producing a bright pigment containing a flaky particle and a metal oxide layer covering a surface of the flaky particle, the method comprising:
    a step (step 1) of adding an aqueous solution of a metal compound to a slurry for forming a metal oxide layer containing the flaky particle and acid to deposit a hydrate of an oxide of a metal derived from the metal compound on the surface of the flaky particle, thereby covering the flaky particle with a metal oxide hydrate layer containing the hydrate of the oxide of the metal; and
    a step (step 2) of washing and drying the flaky particle covered with the metal oxide hydrate layer, and baking the resultant flaky particle covered with the metal oxide hydrate layer to form the metal oxide hydrate layer into a metal oxide layer,
    wherein the metal oxide layer is a single layer formed of at least one material selected from the group consisting of titanium dioxide, reduced titanium oxide, iron oxide, and reduced iron oxide,
    the flaky particle is formed of a material having a refractive index of 1.4 to 1.8,
    the flaky particle has an average thickness of 0.35 μm to 0.55 μm and substantially does not contain a flaky particle having a thickness of 0.15 μm or less, and
    the bright pigment has a particle diameter corresponding to a 90% volume-cumulative particle diameter from a small particle diameter side in a particle size distribution, of 55 μm or less.

12. The method for producing a bright pigment according to claim 11, wherein the flaky particle to be used for preparing the slurry for forming a metal oxide layer contains Na in an amount of 3% by mass or more and less than 9% by mass in terms of a total mass of an oxide ($Na_2O$).

13. The method for producing a bright pigment according to claim 11, wherein the flaky particle has a zeta potential of −20 mV to −10 mV in a hydrochloric acid aqueous solution of pH 2.

14. The method for producing a bright pigment according to claim 11, wherein the aqueous solution of the metal compound is a titanium-containing aqueous solution, and
the titanium-containing solution is an aqueous solution containing at least one selected from the group consisting of titanium tetrachloride, titanium trichloride, titanium dichloride, titanium sulfate, titanyl sulfate, titanium nitrate, and titanyl nitrate.

\* \* \* \* \*

UNITED STATES PATENT AND TRADEMARK OFFICE
CERTIFICATE OF CORRECTION

PATENT NO. : 9,683,105 B2
APPLICATION NO. : 14/363658
DATED : June 20, 2017
INVENTOR(S) : Kitamura Page 1 of 1

It is certified that error appears in the above-identified patent and that said Letters Patent is hereby corrected as shown below:

On the Title Page

Item (72), Column 1, in "Inventors", Line 1, after "Sagamihara" insert -- , Kanagawa --.

Page 2, Item (56), Column 2, under "Foreign Patent Documents", Line 11, delete "JP EP 1524305 A2" and insert -- EP 1524305 A2 --.

Page 2, Item (56), Column 2, under "Other Publications", Lines 3-4, delete "Extended European Search Report issued for corresponding European patent application No. 12856041.4, Mar. 17, 2017, 4 pages.".

In the Specification

Column 13, Line 45, after "less" delete "." and insert -- , --.

Column 14, Line 26, delete "pH2" and insert -- pH 2 --.

Column 14, Line 64, after "3.5" insert -- . --.

Column 21, Line 63, delete "<<Cross" and insert -- <Cross --.

Column 36, Line 15, delete "a (g)" and insert -- a(g) --.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*